US010997699B2

(12) United States Patent
Sekiguchi et al.

(10) Patent No.: US 10,997,699 B2
(45) Date of Patent: May 4, 2021

(54) IMAGE PROCESSING APPARATUS AND IMAGE PROCESSING METHOD

(71) Applicant: CANON KABUSHIKI KAISHA, Tokyo (JP)

(72) Inventors: Hiroyuki Sekiguchi, Kyoto (JP); Kohtaro Umezawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/432,162

(22) Filed: Jun. 5, 2019

(65) Prior Publication Data

US 2019/0287228 A1    Sep. 19, 2019

Related U.S. Application Data

(63) Continuation of application No. PCT/JP2017/044600, filed on Dec. 12, 2017.

(30) Foreign Application Priority Data

Dec. 12, 2016    (JP) .............................. JP2016-240504

(51) Int. Cl.
*G06T 5/00* (2006.01)
*A61B 5/00* (2006.01)
(Continued)

(52) U.S. Cl.
CPC .............. *G06T 5/008* (2013.01); *A61B 5/055* (2013.01); *A61B 8/13* (2013.01); *G06T 1/00* (2013.01);
(Continued)

(58) Field of Classification Search
CPC ........... G06T 5/008; G06T 1/00; A61B 5/055; A61B 8/13
(Continued)

(56) References Cited

U.S. PATENT DOCUMENTS 9,974,439 B2    5/2018    Hirota et al.
2002/0180739 A1*  12/2002  Reynolds ................ G06T 13/20
                                                345/474
(Continued)

FOREIGN PATENT DOCUMENTS

EP    2 415 018 A1    2/2012
JP    2007-301218 A    11/2007
(Continued)

OTHER PUBLICATIONS

Feb. 27, 2018 International Search Report in International Patent Appln. No. PCT/JP2017/044600.
(Continued)

*Primary Examiner* — Hai Tao Sun
(74) *Attorney, Agent, or Firm* — Venable LLP

(57) ABSTRACT

The present invention allows to estimate a continuous surface that defines a boundary surface of an object using image data, even if the image data was acquired by an imaging method in which image information on the boundary surface of the object is limited. An image processing apparatus according to the present invention includes a calculating unit that calculates a brightness gradient of a voxel group constituting volume data which represents a reconstructed image, and an estimating unit that estimates by using the brightness gradient a continuous surface which defines a boundary surface of an object corresponding to the volume data.

23 Claims, 22 Drawing Sheets

(51) Int. Cl.
*G06T 1/00* (2006.01)
*G06T 7/00* (2017.01)
*G06T 15/08* (2011.01)
*G06T 19/00* (2011.01)
*A61B 8/13* (2006.01)
*A61B 5/055* (2006.01)

(52) U.S. Cl.
CPC ............ *G06T 7/0012* (2013.01); *G06T 15/08* (2013.01); *G06T 19/00* (2013.01); *G06T 2200/24* (2013.01); *G06T 2207/10088* (2013.01); *G06T 2207/10132* (2013.01); *G06T 2207/20092* (2013.01); *G06T 2210/41* (2013.01)

(58) Field of Classification Search
USPC ........................................................ 345/424
See application file for complete search history.

(56) References Cited

U.S. PATENT DOCUMENTS

| | | | | |
|---|---|---|---|---|
| 2004/0017370 A1* | 1/2004 | Miyamoto | ............ | G06T 7/0012 345/426 |
| 2005/0046629 A1* | 3/2005 | Jeong | ...................... | G06T 13/20 345/473 |
| 2007/0036411 A1* | 2/2007 | Guetat | ................. | A61B 6/5252 382/128 |
| 2013/0071028 A1* | 3/2013 | Schiller | ................... | G06T 5/003 382/180 |
| 2013/0101189 A1* | 4/2013 | Robitaille | .......... | G01R 33/5608 382/128 |
| 2014/0018682 A1* | 1/2014 | Baba | ...................... | A61B 8/483 600/443 |
| 2014/0350402 A1 | 11/2014 | Hirota et al. | | |
| 2016/0314587 A1* | 10/2016 | Ishikawa | .............. | A61B 5/4312 |
| 2018/0235477 A1 | 8/2018 | Hirota et al. | | |
| 2018/0300959 A1* | 10/2018 | Souza | ...................... | A41H 3/00 |

FOREIGN PATENT DOCUMENTS

| | | |
|---|---|---|
| JP | 2013-188461 A | 9/2013 |
| WO | 2010/113051 A1 | 10/2010 |
| WO | 2012/140984 A1 | 10/2012 |

OTHER PUBLICATIONS

Jun. 18, 2019 International Preliminary Report on Patentability in International Patent Appln. No. PCT/JP2017/044600.

Jun. 26, 2020 European Search Report in European Patent Appln. No. 17880845.7.

G. Guétat, et al., "A Fast Algorithm for Body Extraction in CT Volumes," Medical Imaging 2006: Image Processing, edited by Joseph M. Reinhardt, Josien P. W. Pluim, Proceedings of SPIE, IS & T, vol. 6144, Mar. 15, 2006, pp. 61444C-1-61444C-9.

Demetri Terzopoulos, et al., "Sampling and Reconstruction with Adaptive Meshes," Proceedings of the 1991 IEEE Computer Society Conference on Computer Vision and Pattern Recognition, vol. 3, Jun. 3, 1991, pp. 70-75.

Sarah F.F. Gibson, et al., "A Survey of Deformable Modeling in Computer Graphics," Internet Citation, www.merl.com/report/docs/TR97-19.pdf, Nov. 1, 1997, pp. 1-33.

* cited by examiner

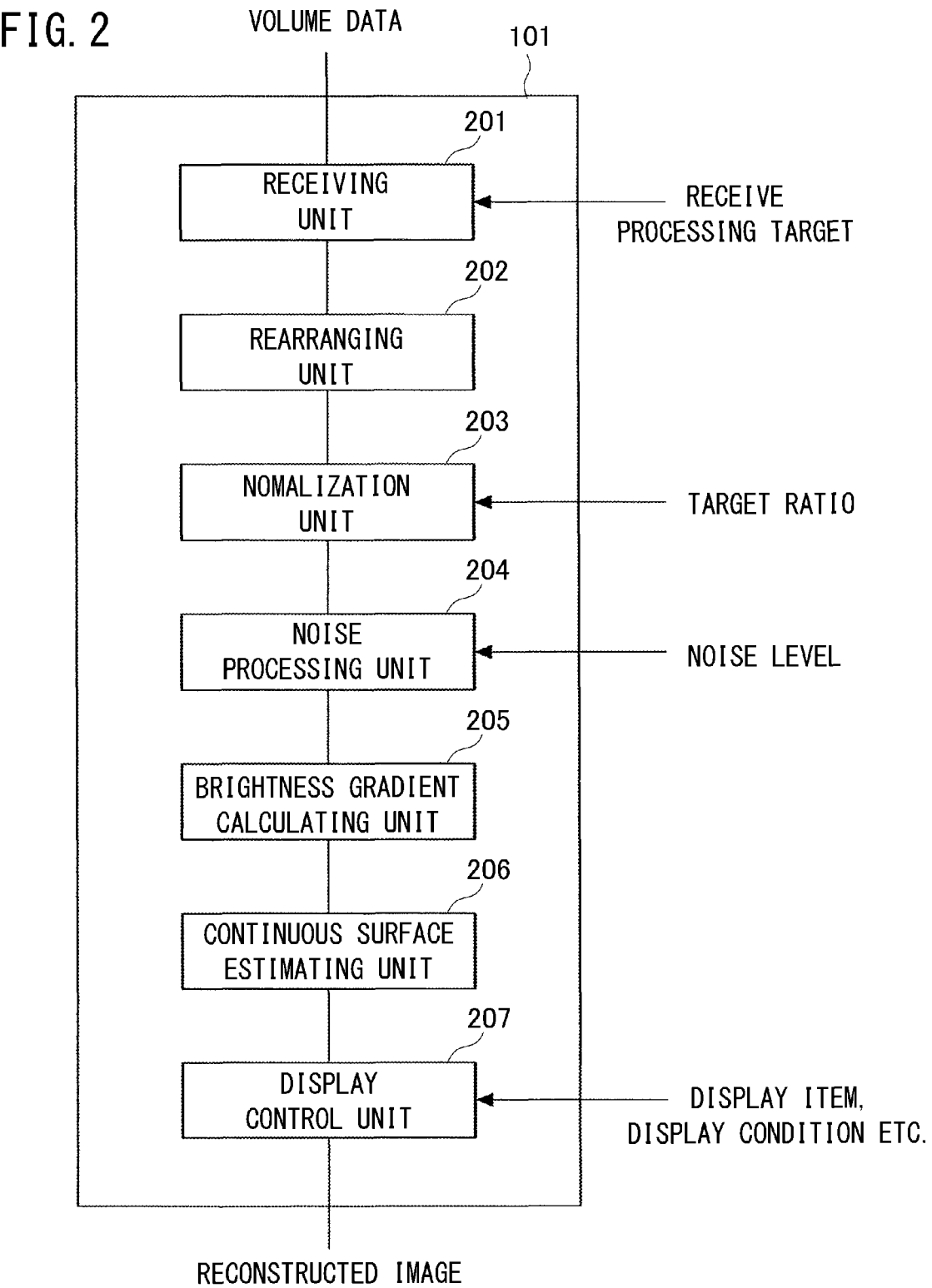

SUPERFICIAL BLOOD VESSEL

DEEP BLOOD VESSEL

BEFORE BOTTOM NOISE REMOVAL

BEFORE BOTTOM NOISE REMOVAL

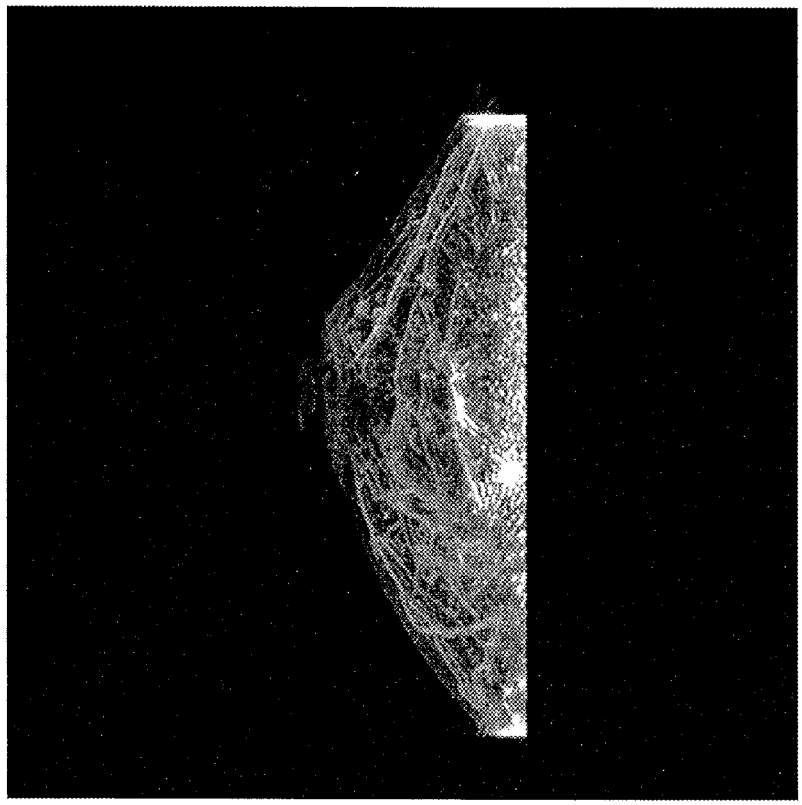
FIG. 22B  AFTER BOTTOM NOISE REMOVAL
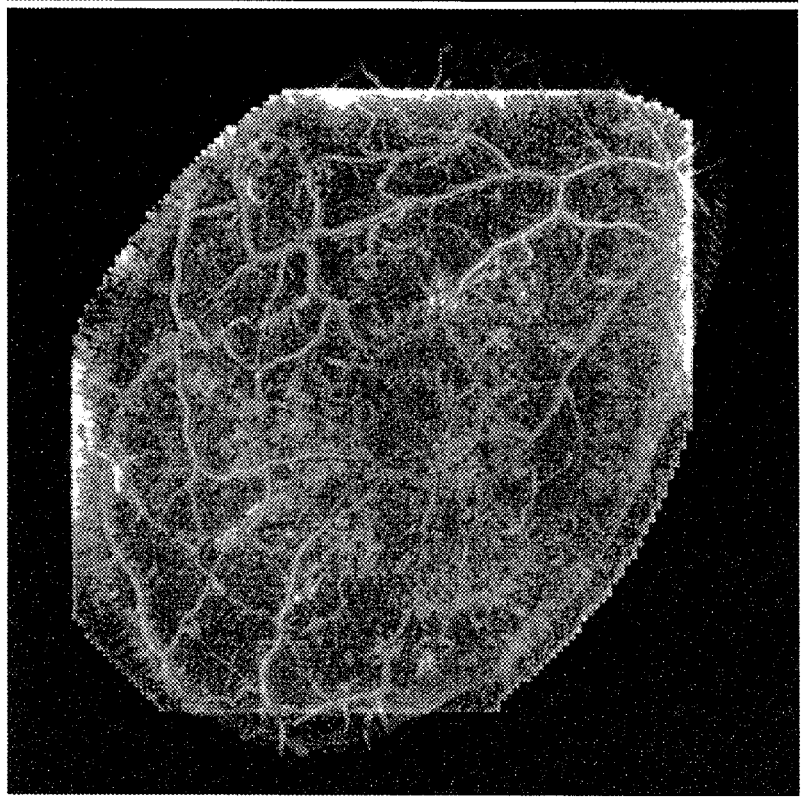
FIG. 22A  AFTER BOTTOM NOISE REMOVAL

IMAGE PROCESSING APPARATUS AND IMAGE PROCESSING METHOD

CROSS-REFERENCE TO RELATED APPLICATIONS

This application is a Continuation of International Patent Application No. PCT/JP2017/044600, filed Dec. 12, 2017, which claims the benefit of Japanese Patent Application No. 2016-240504, filed Dec. 12, 2016, both of which are hereby incorporated by reference herein in their entirety.

BACKGROUND OF THE INVENTION

Field of the Invention

The present invention relates to an image processing apparatus and an image processing method.

Background Art

When an object (e.g. biological tissue) is imaged by the x-ray computed tomography (CT) or the magnetic resonance imaging (MRI), an image of a body surface (e.g skin) of the object is included in the image of the object. In the case of these images, it is relatively easy to generate a body surface by extracting the body surface from the image, and to mask the blood vessels near the body surface (superficial blood vessels), which interrupt image interpretation, since the difference in brightness between the vicinity of the body surface and inside the body is small. In the case of an image captured by the magnetic resonance angiography (MRA), the superficial blood vessels, which interrupt image interpretation, are not captured, hence it is unnecessary to extract the body surface and mask the superficial blood vessels.

On the other hand, in the case of the photoacoustic tomography (PAT) and the ultrasonic image diagnostic method, the brightness inside the body is lower than the brightness in the vicinity of the body surface, hence it is difficult to discern an image inside the body since the high brightness image in the vicinity of the body surface interrupts interpretation. Therefore it is necessary to lower the brightness of the image in the vicinity of the body surface or to eliminate this image. Particularly in the case of a PAT image, the surface is vague and the brightness is high in the blood vessels in the vicinity of the surface, and is low in the blood vessels inside the body. Because of this, manual operation is necessary to remove an image on the surface of the object having a complicated shape, such as a hand, which takes enormous time. If an object (e.g. biological tissue) is imaged by the MRI angiography, the image of the body surface is not captured in the image, or information on the body surface is limited even if the image of the body surface is captured in the image. Therefore even in the case of this type of image, the image of superficial blood vessels is manually removed from the image before image interpretation.

Further, concerning a photoacoustic image, PTL 1 discloses a method of detecting a region in the vicinity of the body surface by defining one line from the body surface of the object in the depth direction, and calculating the distribution of a differential value of the photoacoustic data group that appears on this line.

CITATION LIST

Patent Literature

PTL 1 Japanese Patent Application Publication No. 2013-188461

However, as mentioned above, the operation of manually removing the image of the superficial blood vessels from the image takes a long time. A method disclosed in PTL 1, on the other hand, is a method of detecting an approximate region on the body surface in line units, and the detection result belongs only to the calculation target line. Therefore on the entire body surface, an approximate region can be determined discretely. In other words, a smooth boundary surface on the body surface cannot be determined.

It is an object of the present invention to estimate the boundary surface of the object using image data, even if the image data is acquired by an imaging method in which image information on the boundary surface of the object is limited.

SUMMARY OF THE INVENTION

An example of the present invention according to this description will be described.

An aspect of the invention according to claim 1 is an image processing apparatus having a calculating unit that calculates a brightness gradient of a voxel group constituting volume data which represents a reconstructed image, and an estimating unit that estimates by using the brightness gradient a continuous surface which defines a boundary surface of an object corresponding to the volume data.

An aspect of the invention according to claim 2 is the image processing apparatus according to claim 1, further including a display control unit that displays the continuous surface superimposed on the volume data.

An aspect of the invention according to claim 3 is the image processing apparatus according to claim 1, further including a display control unit that changes a brightness magnification, which is used for displaying the brightness value of each voxel, in accordance with the depth from the continuous surface.

An aspect of the invention according to claim 4 is the image processing apparatus according to claim 3, wherein the display control unit changes the brightness magnification so that all the displayed brightness values of the voxels located in a shallow region are smaller than the maximum value of the displayed brightness values of the voxels located in a deep region.

An aspect of the invention according to claim 5 is the image processing apparatus according to claim 1, wherein the estimating unit applies a physical model, which allows a lattice point group, formed by mutually connecting each lattice point having mass via springs, to freely fall from an area above the object by gravity, to the distribution of the brightness gradient, so as to estimate the continuous surface.

An aspect of the invention according to claim 6 is the image processing apparatus according to claim 5, wherein the estimating unit determines the normal direction of each voxel based on the distribution of the brightness gradient, and uses the normal direction as a direction of resistance that acts on the physical model.

An aspect of the invention according to claim 7 is the image processing apparatus according to claim 1, wherein the estimating unit estimates the continuous surface by processing the voxels having a brightness value exceeding a noise level determined in advance.

An aspect of the invention according to claim 8 is the image processing apparatus according to claim 7, wherein the estimating unit receives specification of the noise level via an input field disposed on a user interface screen.

An aspect of the invention according to claim 9 is the image processing apparatus according to claim 1, further including a display control unit that displays a button, to remove high brightness voxels existing in a deep region of the volume data from the display target, on a user interface screen.

An aspect of the invention according to claim 10 is the image processing apparatus according to claim 1, wherein the volume data is one of photoacoustic tomographic image data, ultrasonic image data and Mill angiographic image data.

An aspect of the invention according to claim 11 is the image processing apparatus according to claim 1, wherein in the case when the voxels constituting the volume data are rearranged in descending order of brightness value, and the ratio of the voxel set on the lower brightness side to the entire voxel data is a predetermined value or less, the estimating unit determines the brightness gradient for brightness values normalized by the maximum brightness values in a voxel set.

An aspect of the invention according to claim 12 is the image processing apparatus according to claim 11, wherein the predetermined value is a value that is at least 99% and not more than 99.99%.

An aspect of the invention according to claim 13 is the image processing apparatus according to claim 1, having a function to display the object, with changing the chromaticity of the voxels in the direction from the continuous surface, which defines the boundary surface of the object, to inside the object.

An aspect of the invention according to claim 14 is an image processing method having: processing that, using a brightness gradient of a voxel group constituting volume data which represents a reconstructed image, estimates a continuous surface which defines a boundary surface of an object corresponding to the volume data; and processing that displays the continuous surface superimposed on the volume data.

An aspect of the invention according to claim 15 is a program that causes a computer to execute: a function, that using a brightness gradient of a voxel group constituting volume data which represents a reconstructed image, estimates a continuous surface which defines a boundary surface of an object corresponding to the volume data; and a function that displays the continuous surface superimposed on the volume data.

According to the present invention, the boundary surface of the object can be estimated using image data, even if the image data is acquired by an imaging method in which image information on the boundary surface of the object is limited. The effects of an invention disclosed in the present disclosure will be now explained.

In the case of the aspect of the invention according to claim 1, the continuous surface, which defines the boundary surface of the object, can be estimated, unlike the case of not using the brightness gradient of the voxel group constituting the volume data which represents a reconstructed image.

In the case of the aspect of the invention according to claim 2, the estimation accuracy can be confirmed, unlike the case of not displaying the continuous surface superimposed on the volume data.

In the case of the aspect of the invention according to claim 3, the target image can be easily interpreted compared with the case of not changing the brightness magnification in accordance with the depth from the continuous surface.

In the case of the aspect of the invention according to claim 4, an image in the deep region can be easily interpreted compared with the case of not making the displayed brightness values of the voxels located in a shallow region smaller than the maximum value of the displayed brightness values of the voxels located in a deep region.

In the case of the aspect of the invention according to claim 5, the estimation accuracy of the boundary surface can be improved with suppressing the influence of markedly different brightness values, compared with the case of not estimating the continuous surface using cloth simulation.

In the case of the aspect of the invention according to claim 6, the estimation accuracy of the boundary surface can be improved with suppressing the influence of markedly different brightness values, compared with the case of not estimating the continuous surface using cloth simulation.

In the case of the aspect of the invention according to claim 7, the estimation accuracy of the continuous surface which defines the boundary surface can be improved, compared with the case of not removing voxels having a noise level determined in advance.

In the case of the aspect of the invention according to claim 8, the estimation accuracy of the continuous surface, which defines the boundary surface, can be adjusted unlike the case of not being able to adjust the noise level.

In the case of the aspect of the invention according to claim 9, the target image can be easily interpreted, unlike the case of not removing the high brightness voxels which appear in a deep region from the display target.

In the case of the aspect of the invention according to claim 10, the continuous surface, which defines the boundary surface of the object, can be estimated, unlike the case of not using the brightness gradient of the voxel group constituting the volume data which represents a reconstructed image.

In the case of the aspect of the invention according to claim 11, an estimation result that does not depend on the voxel data can be acquired, unlike the case of not normalizing the voxel data by the ratio of the level of the brightness value.

In the case of the aspect of the invention according to claim 12, an estimation result that does not depend on the voxel data can be acquired, unlike the case of not normalizing [the voxel data] by the ratio of the level of the brightness value.

In the case of the aspect of the invention according to claim 13, [the object] is displayed with changing the chromaticity of the voxels in the direction from the boundary surface, which is defined by the aspect of the invention according to claim 1, to the inside the object, hence the positional relationship of the tissues and organs existing inside the object from the vicinity of the surface of the object to the inside the object can be easily confirmed.

In the case of the aspect of the invention according to claim 14, the continuous surface, which defines the boundary surface of the object, can be estimated, and the estimation accuracy can also be confirmed, unlike the case of not using the brightness gradient of the voxel group constituting the volume data which represents a reconstructed image.

In the case of the aspect of the invention according to claim 15, the continuous surface, which defines the boundary surface of the object, can be estimated, and the estimation accuracy can also be confirmed, unlike the case of not using the brightness gradient of the voxel group constituting the volume data which represents a reconstructed image.

Further features of the present invention will become apparent from the following description of exemplary embodiments with reference to the attached drawings.

BRIEF DESCRIPTION OF THE DRAWINGS

FIG. 2 is a diagram depicting a functional configuration of the control unit according to the embodiment.

FIG. 22A and FIG. 22B each is a display example of a reconstructed image after removing the bottom noise.

DESCRIPTION OF THE EMBODIMENTS

Embodiments of the present invention will be described in detail with reference to the accompanying drawings.

Embodiment 1

Figure 1:
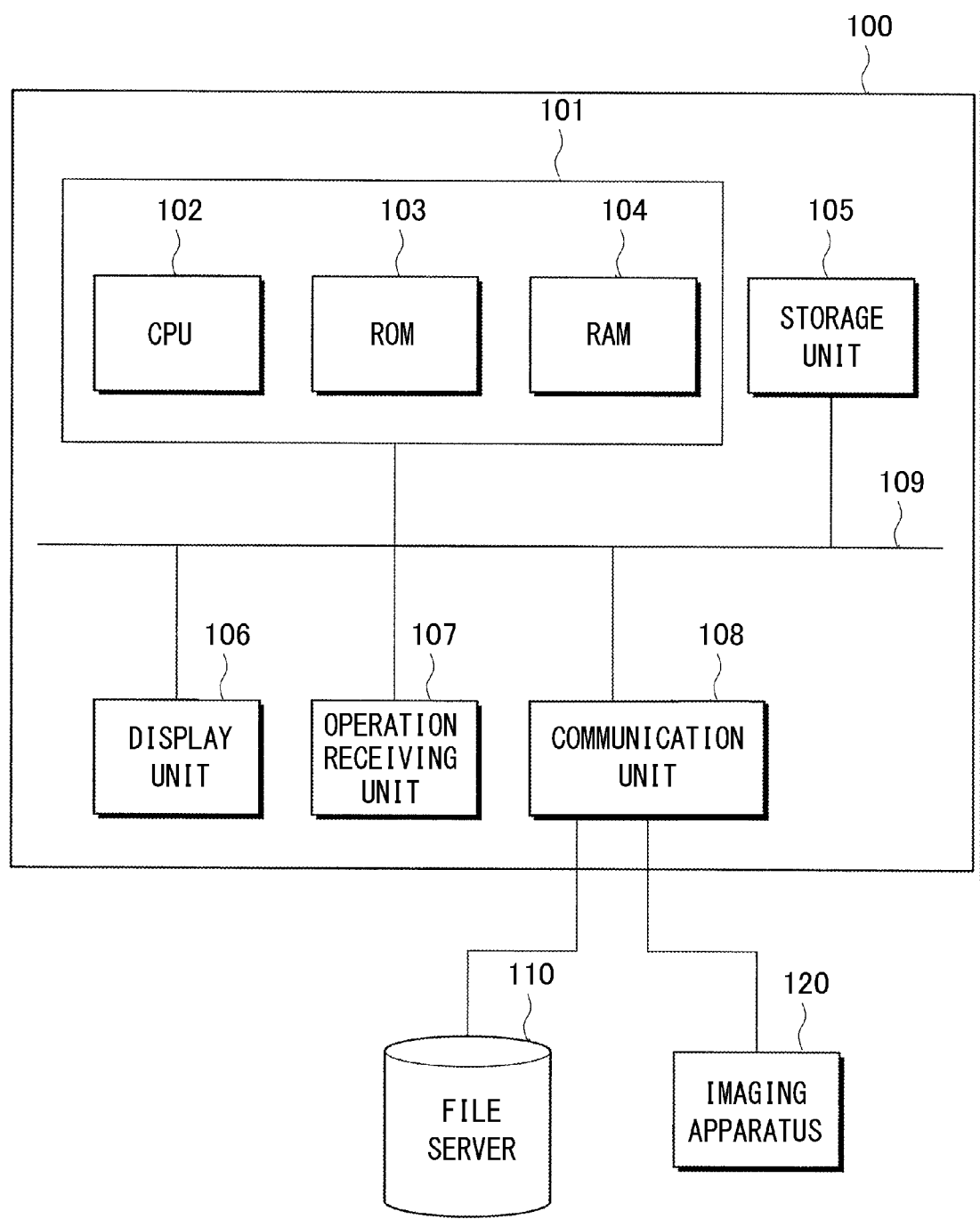
FIG. 1 is a diagram depicting a hardware configuration example of an image processing system which forms and displays a reconstructed image.

<System Configuration>
FIG. 1 is a diagram depicting a hardware configuration example of an image processing system 10 which forms and displays a reconstructed image. The image processing system 10 includes an image processing apparatus 100 which processes three-dimensional image data (volume data) of an object, a file server 110 which stores three-dimensional image data, and tomographic image data used for generating the three-dimensional image data, and an imaging apparatus 120 which performs tomography on an object.

The image processing apparatus 100 includes: a control unit 101 which controls operation of the entire apparatus; a storage unit 105 which stores processing target image data; a display unit 106 which is used for displaying an operation receiving screen and reconstructed images; an operation receiving unit 107 which receives input operation from the user; and a communication unit 108 which communicates with the file server 110 and the imaging apparatus 120. Each of these units is connected via a bus 109, and data is transferred via this bus 109.

The control unit 101 is a computer, and is constituted by: a central processing unit (CPU) 102 which executes programs; a read only memory (ROM) 103 which stores such programs as a basic input/output system (BIOS) and firmware, and data; and a random access memory (RAM) 104 which provides a workspace for programs. The functions which are implemented by the CPU 102 executing programs will be described later.

The storage unit 105 is constituted by a storage device, such as a hard disk device and a semiconductor memory, and stores image data acquired from the file server 110 and the imaging apparatus 120. In Embodiment 1, image data in medical fields are assumed as the image data. The display unit 106 is constituted by a liquid crystal display, for example. The liquid crystal display is constituted by a liquid crystal panel, a backlight and the like. The display unit 106 may be an organic electroluminescence (EL) display.

The operation receiving unit 107 is an input device, such as a mouse and pointing device, which is used for receiving operation input from the user. The communication unit 108 is constituted by a cable interface circuit or a wireless interface circuit.

The file server 110 is a storage device on the network, in which volume data generated by stacking tomographic image data and individual tomographic image data are stored as file data, and is configured by a large capacity hard disk device, for example. The volume data is constituted by an aggregate of voxels (voxel group) which are unit pixels in three-dimensional space. An individual voxel is constituted by coordinate values and a brightness value.

In the file server 110, a tomographic image data, which is outputted from the imaging apparatus 120, for example, is directly stored. Further, in the file server 110, volume data, created in the reconstruction processing (stacking processing of the tomographic image data) by the image processing apparatus 100, may be stored, or volume data created in the reconstruction processing by an image processing apparatus, which is not illustrated, may be stored.

The imaging apparatus 120 is an apparatus that acquires a tomographic image of an object (e.g. biological tissue) by the photoacoustic tomography, the ultrasonic image diagnostic method, the MRI angiography and the like. In Embodiment 1, the image data acquired by each imaging method is called photoacoustic tomographic image data, ultrasonic image data and MRI angiographic image data.

The imaging apparatus 120 corresponding to the photoacoustic tomography is constituted by a light source which irradiates a pulsed laser light to the object, and an ultrasonic probe (probe) which detects an ultrasonic wave from the object. The imaging apparatus 120 corresponding to the ultrasonic image diagnostic method is constituted by an ultrasonic source which irradiates an ultrasonic wave to the object, and an ultrasonic probe (probe) which detects an ultrasonic wave from the object. The imaging apparatus 120 corresponding to the MRI angiography is constituted by a static magnetic field magnet, a gradient coil, an RF coil and a control device.

<Functional Configuration>

FIG. 2 is a diagram depicting a functional configuration of the control unit 101 according to Embodiment 1. The functional configuration depicted in FIG. 2 is implemented by executing programs. The control unit 101 according to Embodiment 1 is constituted by: a receiving unit 201 which receives the processing target volume data; a rearranging unit 202 which rearranges the voxel groups constituting the volume data in descending order of the brightness value; a normalization unit 203 which normalizes each brightness value of the volume data using a reference value, which is the maximum brightness value in the low brightness side voxel set that is extracted so that the ratio of the voxel set, with respect to all voxels, is not more than a predetermined value (e.g. not more than 99.9%); a noise processing unit 204 which removes voxels of which brightness values are not more than the noise level; a brightness gradient calculating unit 205 which calculates the brightness gradient for voxels extracted as a processing target; a continuous surface estimating unit 206 which estimates the continuous surface based on the calculated brightness gradient; and a display control unit 207 which controls the display of the reconstructed image in accordance with the display items and the display conditions.

When the receiving unit 201 receives a processing target file name from the file name list displayed on the screen of the display unit 106, the receiving unit 201 reads the corresponding volume data from the file server 110, and executes the processing function to store the volume data to the storage unit 105. The rearranging unit 202, using a known method, executes the processing function to rearrange the voxel groups constituting the volume data in descending order of the brightness value.

The normalization unit 203 is a function unit that, when the ratio of a number of voxels constituting the lower brightness side voxel set, with respect to a number of all voxels, is a target ratio (e.g. 99.9%) which is received via an operation screen (not illustrated), normalizes the brightness values of all the voxels so that the maximum brightness value of the voxel set on the lower brightness side is converted into a reference value (e.g. 1.0). The normalization processing is executed in order to standardize the processing functions in subsequent stages, regardless the difference in the brightness distribution of the processing target volume data. An example of the operation screen which is used for inputting the reference value will be described later.

The noise processing unit 204 executes the processing function that extracts, as the processing target, only the voxels, which have brightness values exceeding the noise level received via the operation screen (not illustrated). In other words, the noise processing unit 204 executes the processing function that removes voxels of which brightness values are not more than the noise level. The noise level used as the threshold is inputted by the user via the operation screen (not illustrated), for example. The brightness gradient calculating unit 205 executes the processing function that calculates the brightness gradient for the voxels extracted as the processing target (described in detail later).

Figure 3A:
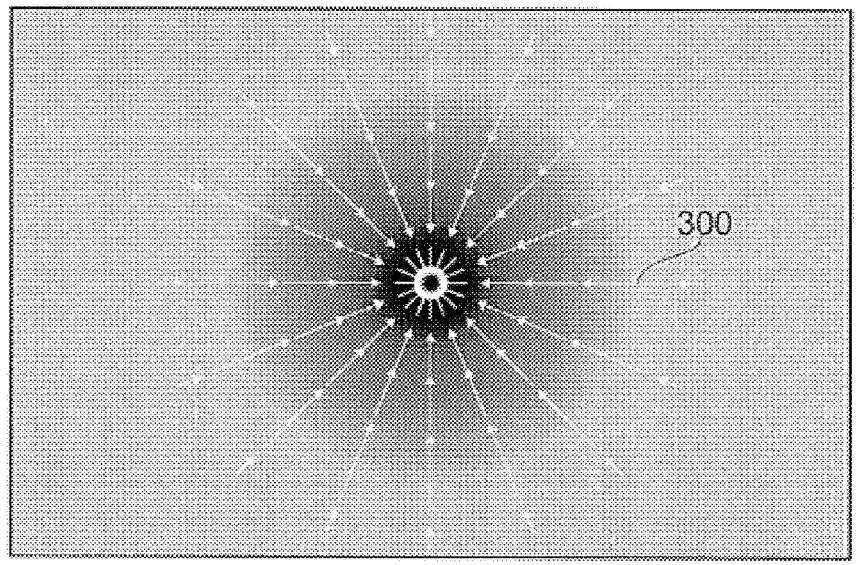
FIGS. 3A and 3B each is a diagram for describing an image of brightness gradient.
Figure 3B:
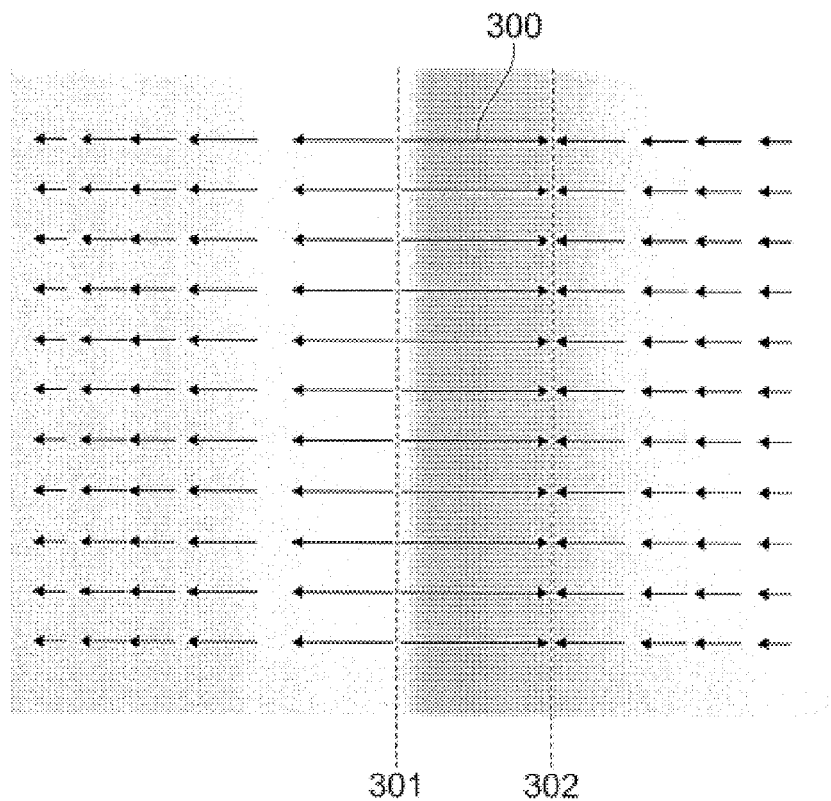

The brightness gradient is a vector quantity expressed by the magnitude of the gradient, which indicates the maximum brightness difference between an individual voxel and the voxels located surrounding (adjacent to) the voxel, and the direction of the gradient, which indicates the direction in which the maximum brightness difference is acquired. Here the surrounding range (number of pixels) is provided in advance, and the minimum value thereof is "1". FIG. 3A and FIG. 3B are diagrams for describing an image of the brightness gradient 300. In FIG. 3A and FIG. 3B, a position having a high brightness value is expressed by white, and a position having a low brightness value is expressed by black.

The length of each vector in FIG. 3A and FIG. 3B indicates the magnitude of the brightness gradient at each position, and the direction of the vector indicates the direction of the brightness gradient 300 at each position. FIG. 3A indicates a brightness gradient 300 in the case where the brightness values decrease concentrically toward the center at which the brightness is lowest. FIG. 3B indicates the brightness gradient 300 in the case where the brightness changes between the left side and the right side of the line 301. The left side of the line 301 indicates the brightness gradient 300 where the brightness value is highest at the position of the line 301, and decreases in the left direction. The right side of the line 301, on the contrary, indicates a case when the brightness changes in the opposite direction with respect to the position of the line 302.

The brightness gradient 300 may be calculated for all the voxel groups constituting the volume data, or may be calculated only for the voxel groups scattered on the surface layer portion of the volume data. In the case of calculating the brightness gradient only for the surface layer portion of the volume data, the continuous surface that can be estimated is limited to the body surface, but the calculation amount decreases and the processing time is shortened. In the case of determining a continuous surface which defines the boundary surface of the internal structure, however, at least the voxels at the depth where the boundary surface is more likely to exist are also included in the calculation targets.

The continuous surface estimating unit 206 executes the processing function to estimate the continuous surface based on the calculated brightness gradient 300 (described in detail later). If the brightness gradient 300 indicates the form of the boundary surface accurately and the brightness gradient 300 is in an ideal state without excess or insufficiency, the continuous surface estimating unit 206 can directly reproduce the form of the boundary surface from a set of the brightness gradient 300, but in the case of the processing target volume data of Embodiment 1, there is no or very little information on the body surface of the object. In other words, most of the brightness values that can be used in the surface layer portion of the volume data originates from the superficial blood vessels and noises.

Therefore the continuous surface estimating unit 206 according to Embodiment 1 executes a processing function to estimate the body surface of the object as a form that appears when the surface of the volume data is covered with cloth. In other words, according to Embodiment 1, "cloth simulation" is applied to the volume data. Cloth simulation is a simulation in which the lattice point group, where the lattice points having mass are interconnected by springs, is regarded as cloth, and the form of the cloth, when the cloth is allowed to fall freely from an area above the object by gravity, is estimated.

Figure 4:
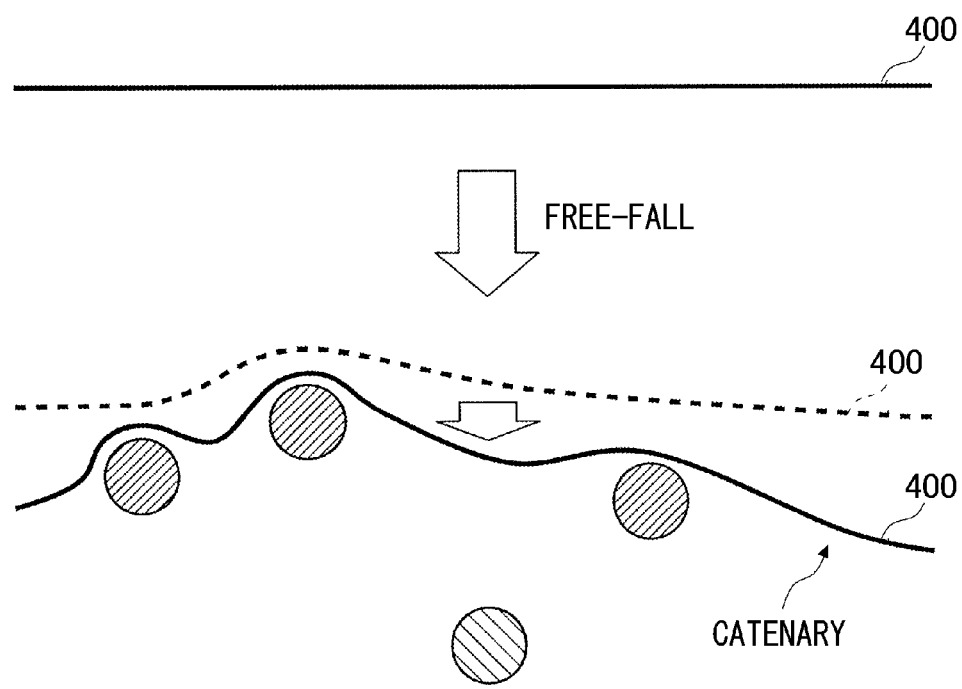
FIG. 4 is a diagram for describing cloth simulation.

FIG. 4 is a diagram for describing the cloth simulation. In FIG. 4, the cloth model 400 is disposed in a position above the superficial blood vessels and deep blood vessels, which indicate high brightness values in the voxel data, and then the cloth model 400 is allowed to fall freely. When this physical model is applied, the cloth model 400 deforms such that a catenary is formed between a superficial blood vessel and a superficial blood vessel. In Embodiment 1, the surface formed by the cloth model 400 is regarded as the body surface of the object.

Figure 5:
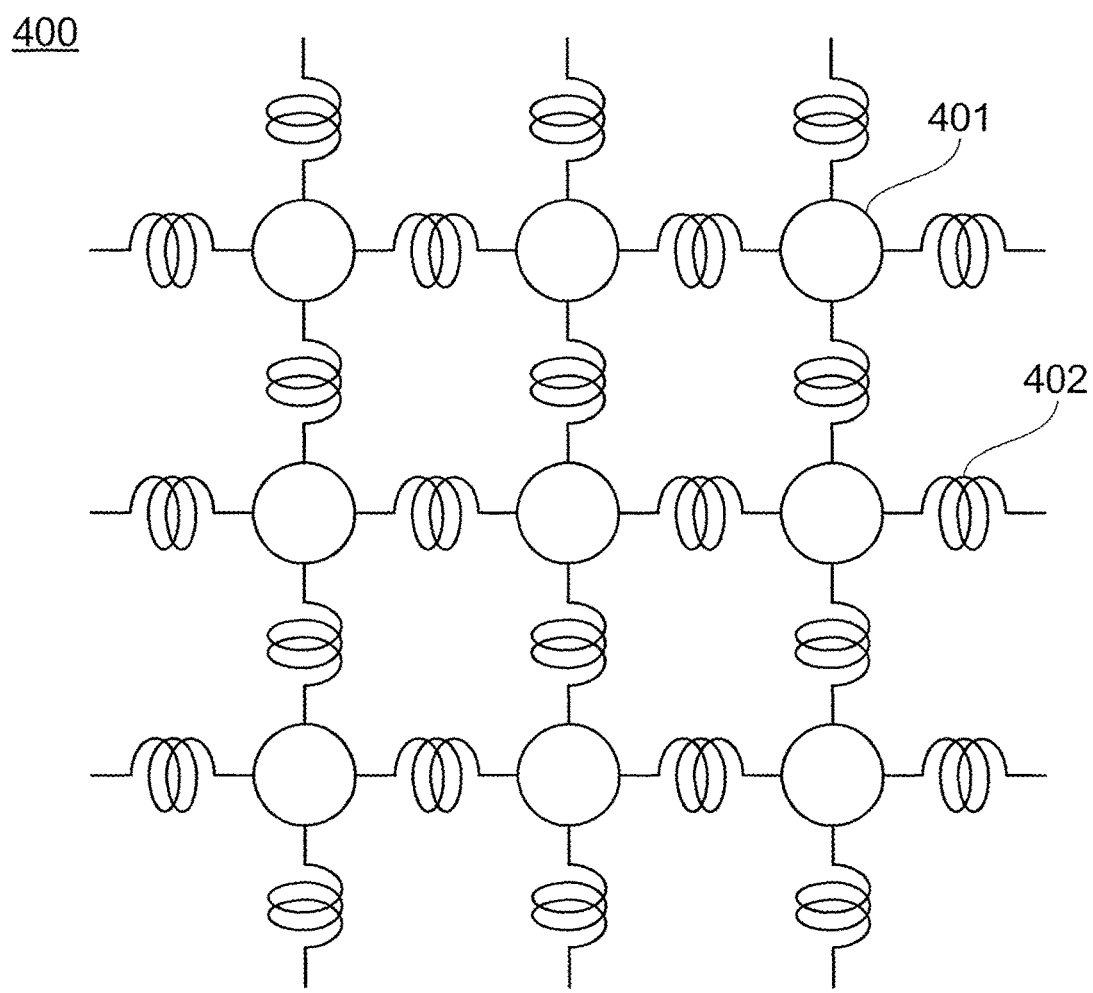
FIG. 5 is a diagram for describing a configuration example of a cloth model.

FIG. 5 is a diagram for describing a configuration example of a cloth model 400. In FIG. 5, the cloth model 400 is a spring-node model. A circle in FIG. 5 is a node 401 having mass, and each node 401 is interconnected via the springs 402. Node here is an example of a lattice point. FIG. 5 is an example of disposing only structural springs, but shear springs may be added in the diagonal directions. In Embodiment 1, the in-plane density of the nodes 401 is smaller than the in-plane density of the voxels constituting the voxel data. In other words, in a certain area, more voxels exist than the nodes 401. This means that the node 401 is always contacting any one of the voxels.

Figure 6:
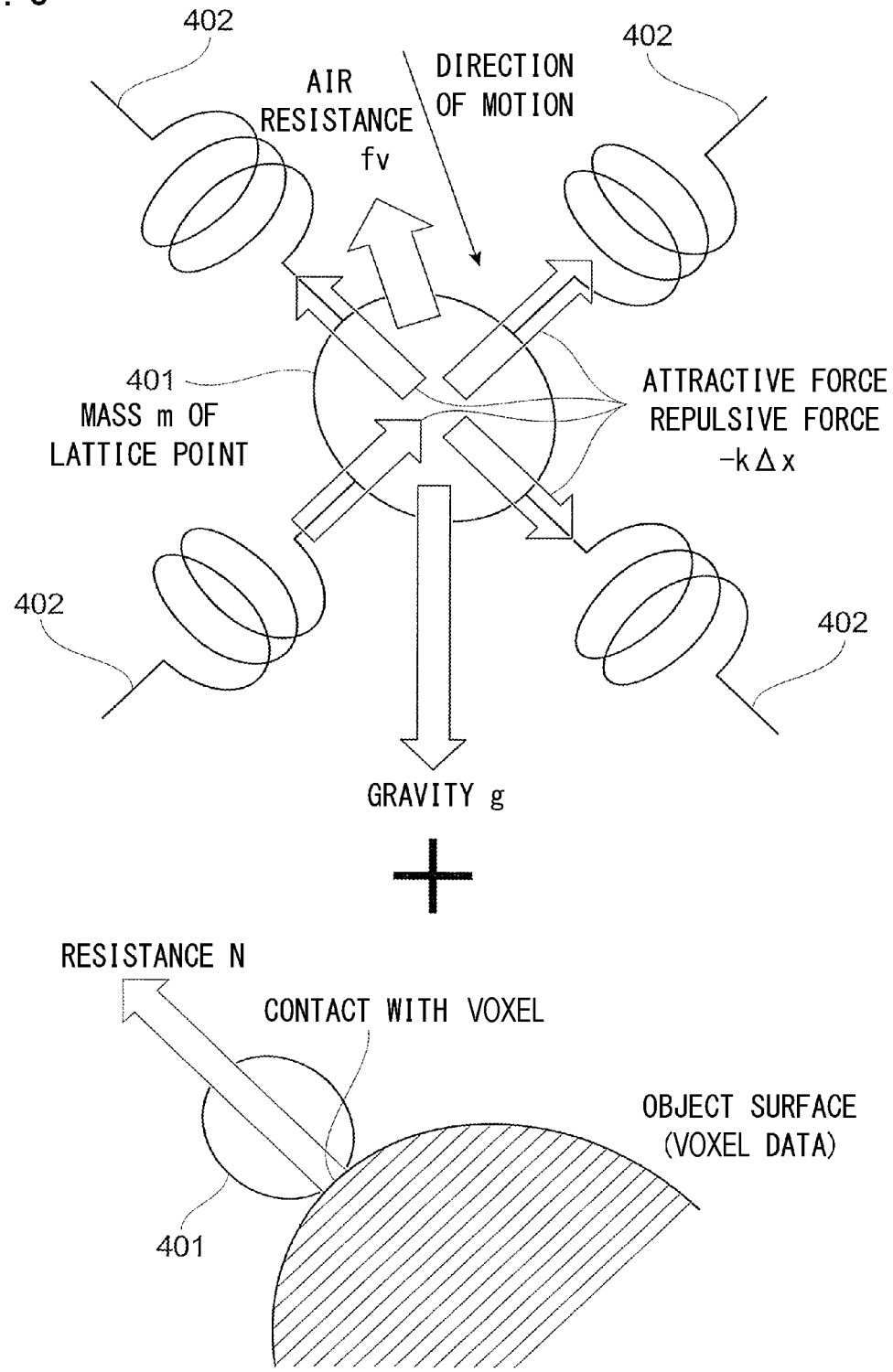
FIG. 6 is a diagram for describing a force that acts on each node that is required for calculation of the cloth simulation.

FIG. 6 is a diagram for describing a force that acts on each node 401 that is required for calculation of the cloth simulation. The cloth simulation requires: air resistance fv that acts in the opposite direction of the direction of motion; gravity g that acts on the node 401 having mass m; attractive force or repulsive force $-k\Delta x$ which acts with peripheral nodes 401; and resistance N which the node 401 receives from contact with a voxel. To calculate a direction in which the resistance N acts, the above mentioned gradient direction of the brightness gradient 300 is used. In concrete terms, the direction of the brightness gradient 300, calculated for the voxel when the node 401 contacts, is used as a normal direction of the object surface which determines the direction in which the resistance N acts. The information on the speed and position to stop the deformation of the cloth model 400 is provided via the operation receiving unit 107.

Figure 7:
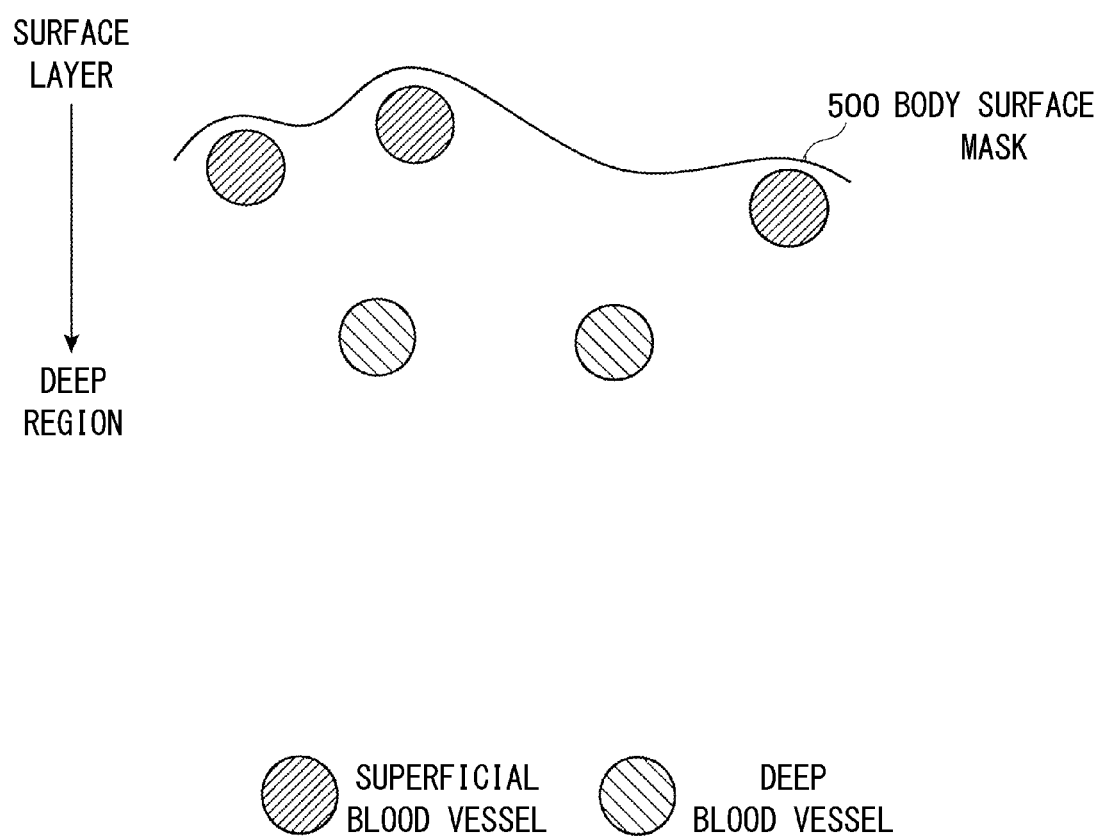
FIG. 7 is a diagram for describing a body surface mask, which is a continuous surface estimated by the cloth simulation described in the embodiment.

FIG. 7 is a diagram for describing a body surface mask 500, which is a continuous surface estimated by the cloth simulation described in Embodiment 1. In the case of Embodiment 1, the cloth simulation is applied using the brightness values which originated from the superficial blood vessels, instead of the body surface, and a body surface mask 500 which changes along the superficial blood vessels is acquired. Because of the nature of the cloth simulation, a markedly different point (voxel) of which brightness value or the like is very different from the peripheral voxels is ignored. As a result, the body surface mask 500 is determined as the continuous surface in which high brightness voxels, which discretely appear in the surface layer surface, are connected by catenaries.

Figure 8:
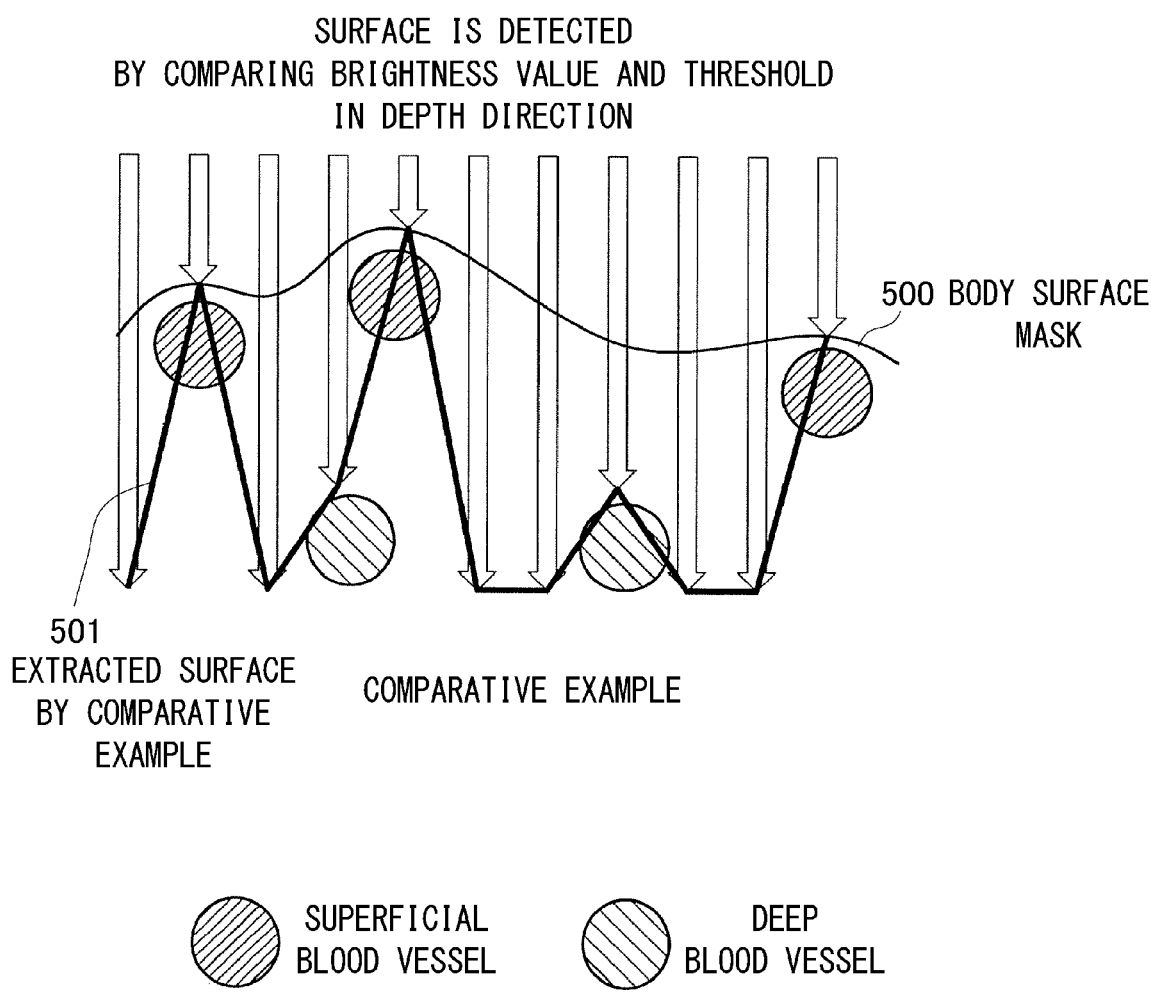
FIG. 8 is a diagram for describing an example of a surface extracted by a comparative example.

FIG. 8 is a diagram for describing an example of a surface extracted according to a comparative example. The comparative example indicates an example of an extracted surface 501 which is generated by comparing the brightness value of each voxel and a threshold linearly in the depth direction, and connecting voxels having a brightness value exceeding the threshold. In the comparative example, both the voxels in the superficial blood vessels and the deep blood vessels are detected as voxels having brightness values exceeding the threshold, hence the extracted surface 501 has a form that is not similar to the body surface.

Figure 9:
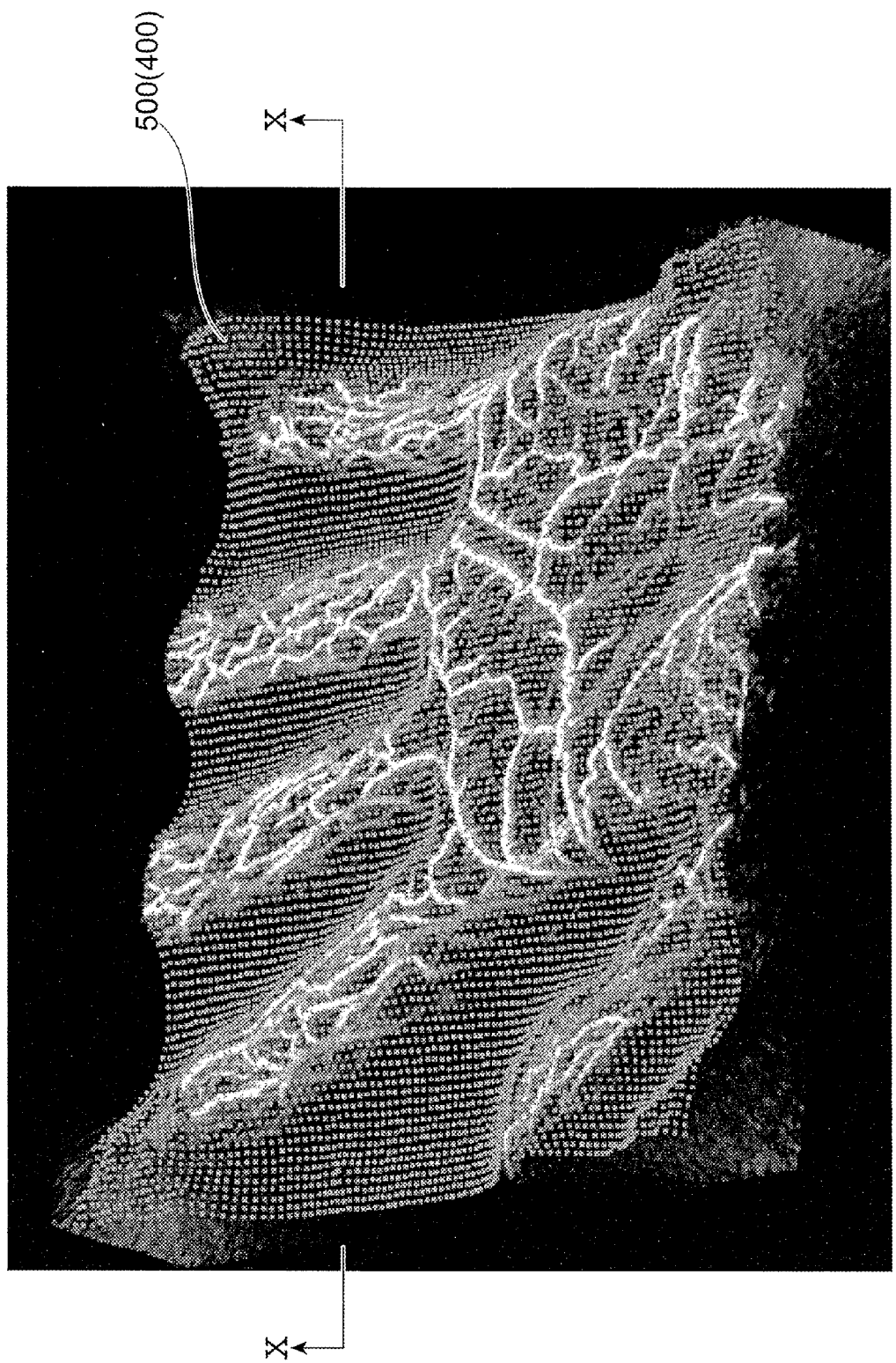
FIG. 9 is a screen example in which volume data acquired by imaging a palm by photoacoustic tomography and the body surface mask are superimposed and displayed.

For reference, an example of the body surface mask 500 generated by the cloth simulation is described. FIG. 9 is a screen example in which volume data acquired by imaging a palm by the photoacoustic tomography and the body surface mask 500 are superimposed and displayed. In FIG. 9, the body surface mask 500, which represents the continuous surface, is expressed by nodes 401 (see FIG. 5) of the cloth model 400 that is used for generating the body surface mask 500, so that the internal structure can be observed. The cloth model 400, indicated in FIG. 9, is constituted by about 10,000 (101×101) nodes 401.

Figure 10:
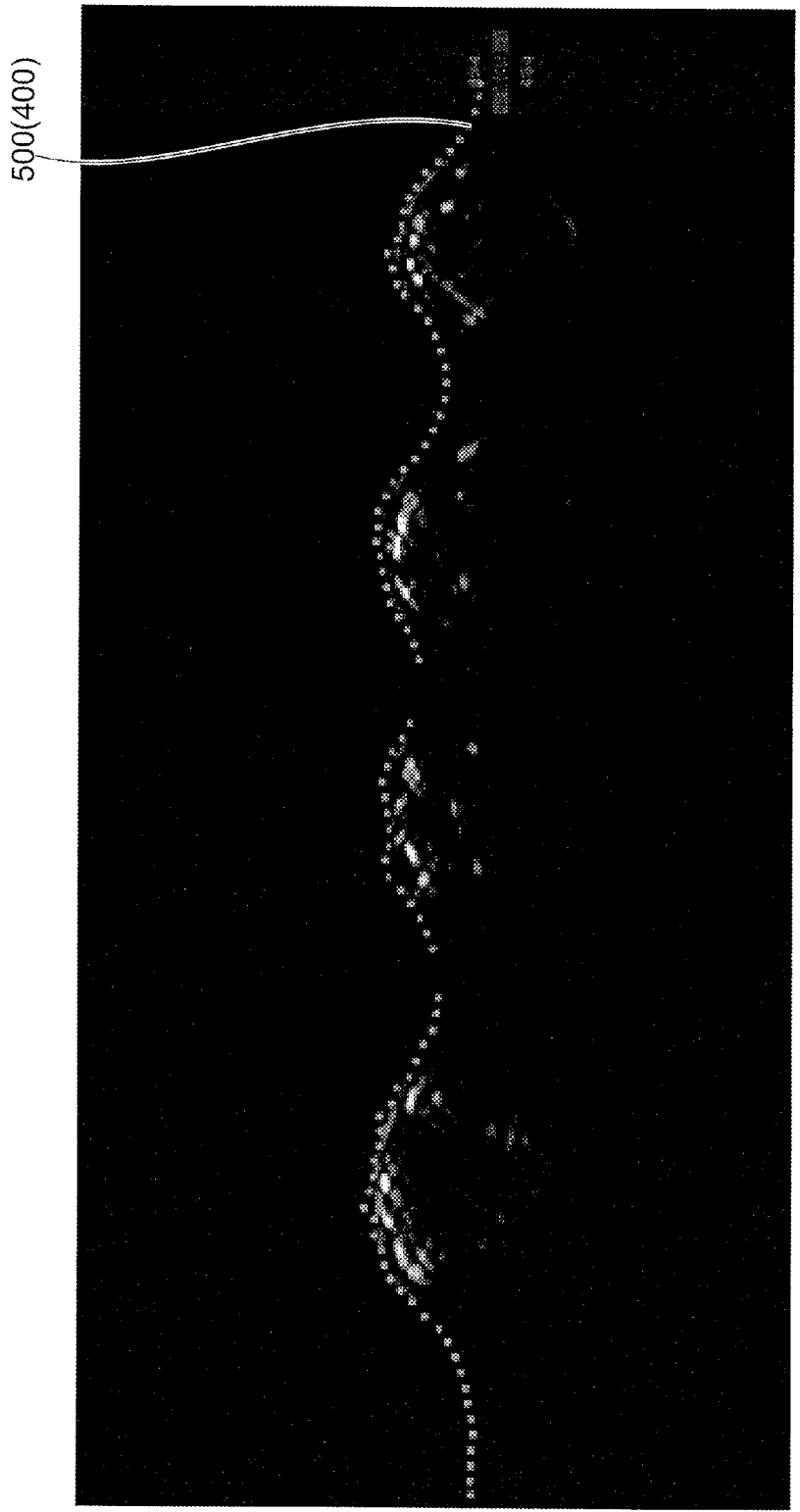
FIG. 10 is a cross-sectional view for describing a positional relationship between the superficial blood vessels and the body surface mask sectioned at X-X in FIG. 9.

FIG. 10 is a cross-sectional view for describing a positional relationship between the superficial blood vessels and the body surface mask 500 sectioned at X-X in FIG. 9. The X-X cross-section is positioned so that four fingers cross horizontally. Therefore the body surface mask 500 in FIG. 10 is curved along the shape of the body surface in the finger portions, and forms catenaries between the fingers.

Figure 11:
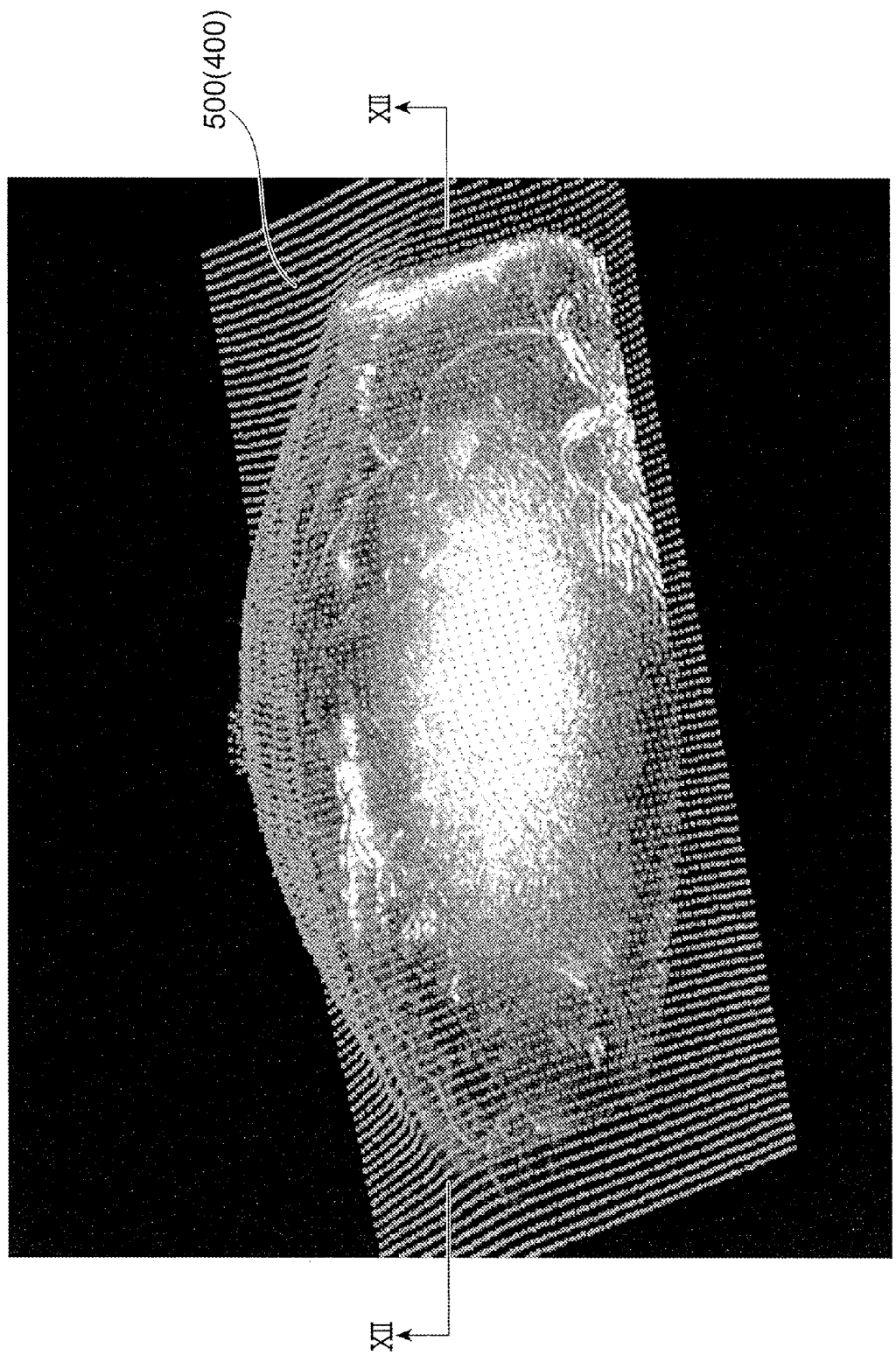
FIG. 11 is a screen example in which volume data, acquired by imaging a breast by photoacoustic tomography and the body surface mask, are superimposed and displayed.

FIG. 11 is a screen example in which the volume data acquired by imaging a breast by the photoacoustic tomography and the body surface mask 500 are superimposed and displayed. In the case of FIG. 11 as well, the body surface mask 500 is expressed by the nodes 401 of the cloth model 400 that is used for generating the body surface mask 500 so that the internal structure can be observed. The cloth model 400 in FIG. 11 as well is constituted by about 10,000 (101×101) nodes 401.

Figure 12:
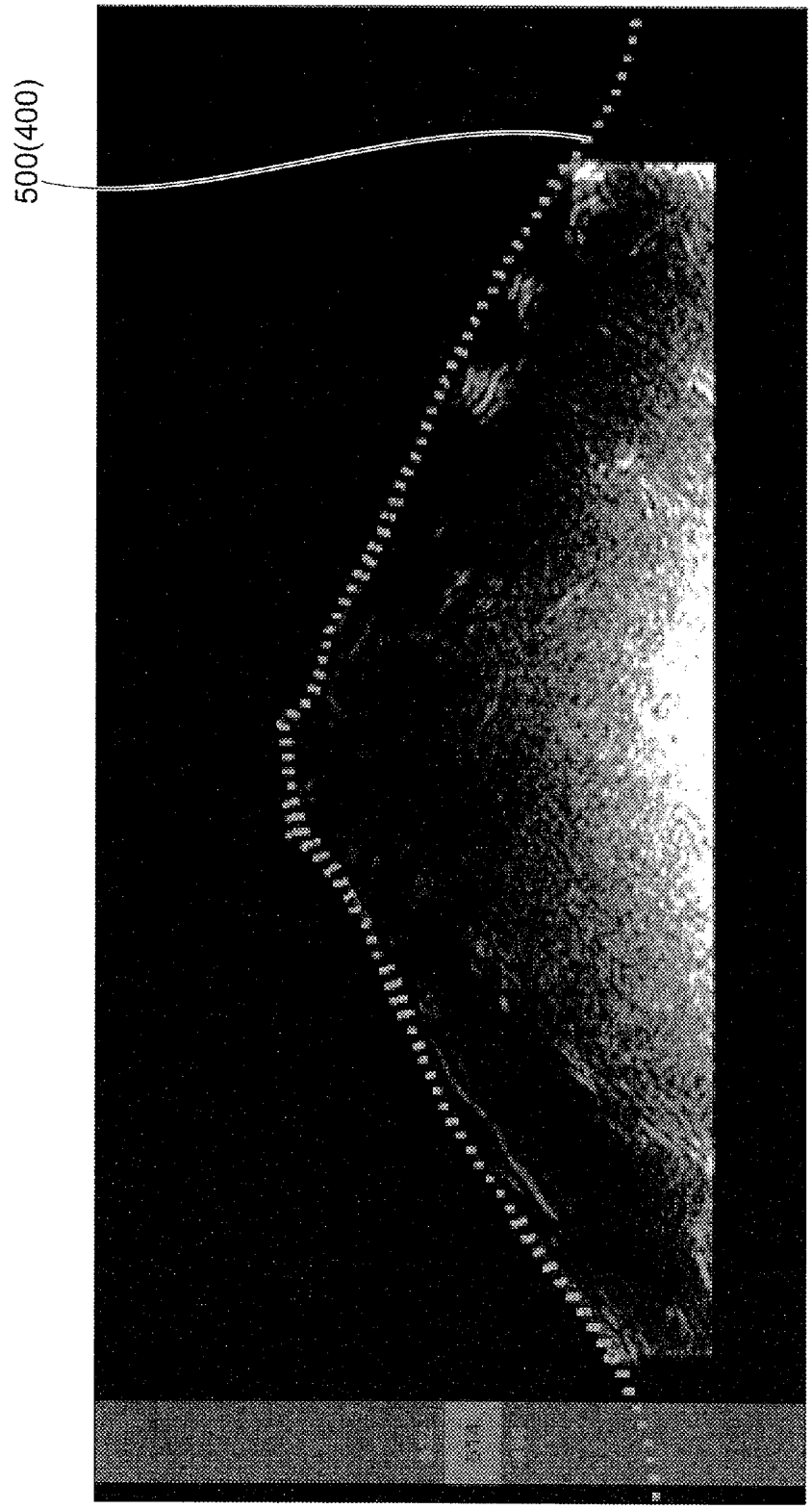
FIG. 12 is a cross-sectional view for describing a positional relationship between the superficial blood vessels and the body surface mask sectioned at XII-XII in FIG. 11.

FIG. 12 is a cross-sectional view for describing a positional relationship between the superficial blood vessels and the body surface mask 500 section at XII-XII in FIG. 11. The XII-XII cross-section is positioned so that the breast is crossed in the thickness (height) direction. Therefore the body surface mask 500 in FIG. 12 is curved along the shape of the body surface of the breast. In the case of FIG. 11 and FIG. 12, many noises (bottom noises) that interfere with the image interpretation are included in the bottom surface (deep region) of the breast. The display function to remove these noises will be described later.

The display control unit 207 corrects the reconstructed image in accordance with the display items and the display conditions which are inputted via the operation receiving unit 107, and executes the processing function displayed on the display unit 106. For the display items, the estimated continuous surface, superficial blood vessels (veins), deep blood vessels (arteries), noises generated on the bottom surface and the like can be specified (described in detail later). Instructions for display of these display targets are specified via the later mentioned user interface screen.

For the display conditions, a noise level that generates the maximum value in the brightness level ranges not used for display, a color coded display for the superficial blood vessels and deep blood vessels, a ratio of voxels in the surface layer region and voxels in the deep region with respect to the reconstructed image, a highlight display of the superficial region and highlight display of the deep region (setting brightness magnification in accordance with the depth in Embodiment 1) and the like can be specified. Instructions for these conditions are specified via the later mentioned user interface screen.

<Example of User Interface Screen>

Figure 13:
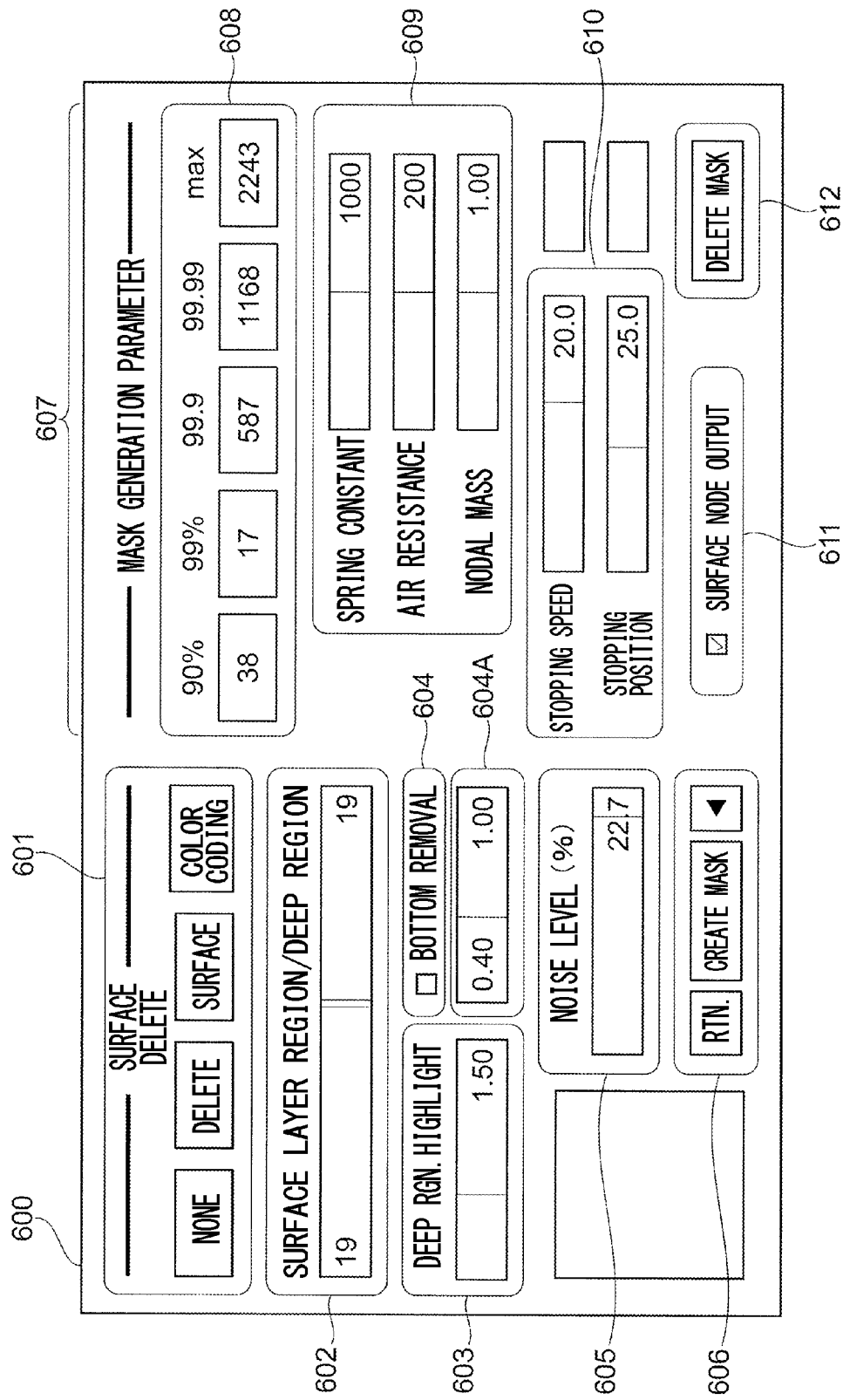
FIG. 13 is a diagram depicting an example of a user interface screen displayed on the display unit.

FIG. 13 is a diagram depicting an example of a user interface screen 600 displayed on the display unit 106. The user interface screen 600 is constituted by a plurality of fields created for inputting the above mentioned display items and display conditions.

A surface delete field 601 is used to select the blood vessel display mode. The surface delete field 601 indicated in FIG. 13 includes: "NO (NO delete)" which indicates that the superficial blood vessels are displayed; "Delete" which indicates that the superficial blood vessels are deleted from the display screen; "Surface" which indicates that only the superficial blood vessels and displayed; and "Color coded" which indicates that the superficial blood vessels and deep blood vessels are color coded and displayed. In the case of Embodiment 1, the superficial blood vessels and the deep blood vessels are distinguished by a number of pixels (voxels) in the direction from the position of the body surface mask 500 toward the deep region. In other words, the chromaticity of the voxels may be changed from the continuous surface (e.g. body surface mask 500) which defines the boundary surface of the object toward inside the object. In the case of color coding depending on the depth from the surface, it is preferable to color code in accordance with the shortest distance from the body surface mask 500 in the normal direction.

For example, it is assumed that a range of 10 voxels from the body surface mask 500 in the depth direction is the surface layer region, and high brightness voxels belonging to the surface layer regions are the superficial blood vessels. Further, a range exceeding 30 voxels from the body surface mask 500 in the depth direction is the deep region, and high brightness voxels belonging to the deep region are deep blood vessels.

A surface layer region/deep region field 602 is used to input the display ratio between the voxels belonging to the surface layer region and the voxels belonging to the deep region. In the case of the example of the surface layer region/deep region field 602 in FIG. 13, the ratio between the voxels belonging to the surface layer region and the voxels belonging to the deep region is changed by moving a slider.

A deep region highlight field 603 is used to specify the degree of highlight display of the deep region. The numeric value in this field indicates the brightness coefficient by which the brightness value of a voxel belonging to the deep region is multiplied. In the case of FIG. 13, the brightness coefficient is "1.50". A bottom removal field 604 is used to remove the high brightness voxels that appear in the bottom (bottom surface) region of the volume data, from the display targets. In the case of FIG. 13, the high brightness voxels in the bottom region are removed from the display targets if there is a check in the check box.

A brightness magnification setting field 604A is used to set the brightness magnification by which the brightness value of a voxel belonging to the surface layer region is multiplied, and the brightness magnification by which the brightness value of a voxel belonging to the deep region is multiplied. In the case of FIG. 13, "0.40" is a brightness coefficient that is applied to the surface layer region, and "1.00" is a brightness coefficient that is applied to the deep region. In the case of the example in FIG. 13, the display brightness of a voxel belonging to the surface layer region is smaller than the original brightness value, and the display brightness of a voxel belonging to the deep region is the same as the original brightness value.

A noise level field 605 is used to specify a value of the brightness value that is processed as a noise level. By setting the noise level appropriately, the estimation accuracy of the body surface mask 500 can be increased. In the case of the example in FIG. 13, the ratio of the voxels on the lower brightness side, which is handled as the noise level, is set as a percentage. The maximum value of the brightness value that is handled as the noise level may be set here instead. In the case of Embodiment 1, the user can adjust the noise level. By appropriately adjusting the noise level, the estimation accuracy of the body surface mask 500 can be adjusted.

A create mask field 606 is used to create the body surface mask 500. When the "Mask creation" button is pointed to and clicked on, the above mentioned processing of the brightness gradient calculating unit 205 and the continuous surface estimating unit 206 are executed.

A mask generation parameter field 607 is an input field that is used to generate the body surface mask 500, and is constituted by some input fields to be described below. A target ratio field 608 is used to input the target ratio that is used for the normalization processing. In the case of the example in FIG. 13, "99.9%" is specified as a ratio of a number of voxels on the low brightness side after rearranging the voxels in descending order of brightness value with respect to the total number of voxels. The inventors confirmed by experiments that a good display result is acquired when the target ratio is 99.9%, but it is preferable that this value can be adjusted in the range of 99% to 99.9%.

A cloth simulation parameter field 609 is used to input the spring constant, the air resistance and the nodal mass, which are used for the cloth simulation. In the case of the example in FIG. 13, the "spring constant" is "1000", the "air resistance" is "200", and the "nodal mass" is "1.00".

A stopping condition field 610 is used to input the stopping speed and the stopping position. These items set the conditions to end the cloth simulation, that is, the conditions to stop the vibrating operation. A surface node output field 611 is used to specify whether or not the body surface mask 500 is displayed superimposed on the volume data that represents the reconstructed image. In the case of FIG. 13, if there is a check in the check box, the body surface mask 500 is displayed superimposed on the reconstructed image. In this case, the screen, on which the body surface mask 500 is displayed superimposed on the reconstructed image, as indicated in FIG. 9 and FIG. 11, is displayed. By displaying the created body surface mask 500 superimposed on the reconstructed image, the user can confirm whether or not the estimation result of the body surface mask 500 is appropriate. A delete mask button 612 is used to delete the body surface mask 500, which is displayed superimposed on the volume data, from the display targets.

<Processing Operation>

Figure 14:
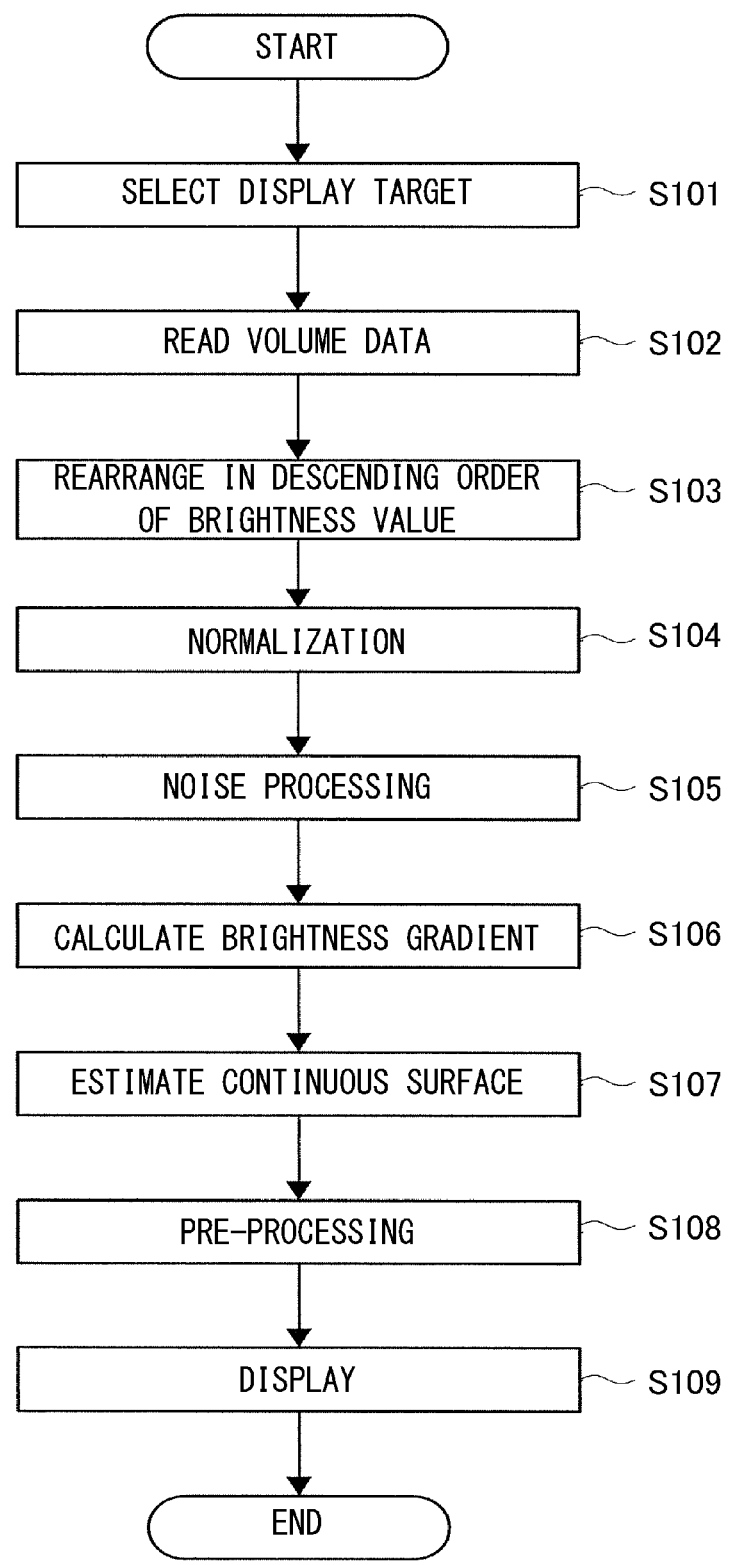
FIG. 14 is a flow chart depicting the image processing procedure by the control unit of the embodiment.

A processing operation of the image processing apparatus 100 according to Embodiment 1 will be described. FIG. 14 is a flow chart depicting the image processing procedure by the control unit of Embodiment 1.

The control unit 101 receives the selection of the processing target file name using the function of the receiving unit 201 (step 101). Then, from the file server 110, the control unit 101 reads the volume data corresponding to the selected file name (step 102). This processing corresponds to the processing that acquires image data of the object including the structure. Then using the function of the rearranging unit 202, the control unit 101 rearranges the voxel groups constituting the read voxel data in descending order of brightness value (step 103).

Then the control unit 101 normalizes the rearranged volume data using the function of the normalization unit 203 (step 104). In the normalization processing, the brightness values of all the voxels are converted so that the maximum brightness value in the voxel set on the lower brightness side that satisfies the target ratio is converted into the reference value. By this normalization processing, the estimation accuracy of the body surface is maintained high, regardless the difference of the brightness distribution of the voxels constituting the volume data.

Then using the function of the noise processing unit 204, the control unit 101 extracts only voxels having brightness values exceeding the noise level from the normalized voxel data as the processing target (step 105). This processing corresponds to the processing that acquires information which indicates the position of the structure by performing the image processing for the image data. Then using the function of the brightness gradient calculating unit 205, the control unit 101 calculates the brightness gradient for each of the voxels extracted as the processing target (step 106).

Then using the function of the continuous surface estimating unit 206, the control unit 101 estimates the continuous surface (body surface mask 500 in the case of Embodiment 1), which defines the body surface of the object (step 107). This processing corresponds to the processing that estimates a boundary surface of the object by the processing using the information which indicates the position of the structure. In the case of Embodiment 1, the brightness gradient calculated in step 106 is used as one of the parameters of the cloth simulation, and the cloth simulation is executed for the voxel data, whereby the body surface mask 500, covering the superficial blood vessels, is estimated. In this way, in the processing that the boundary surface of the object is estimated, the image data (brightness gradient of the image data in this case) may be used, in addition to the information that indicates the position of the structure.

Then using the function of the display control unit 207, the control unit 101 pre-processes the reconstructed image so that the display contents match with the items and conditions specified on the user interface screen 600 described above (step 108). For the pre-processing, processing to remove only specific blood vessels from the display target and processing to add colors, for example, are executed. Further, for the pre-processing, processing to display the body surface mask 500 superimposed on the reconstructed image is executed. After the pre-processing, the control unit 101 displays the reconstructed image on the display unit 106 (step 109).

<Display Screen Examples>

Display screen examples implemented using the user interface screen 600 will be described.

<Screen Example 1>

Figure 15:
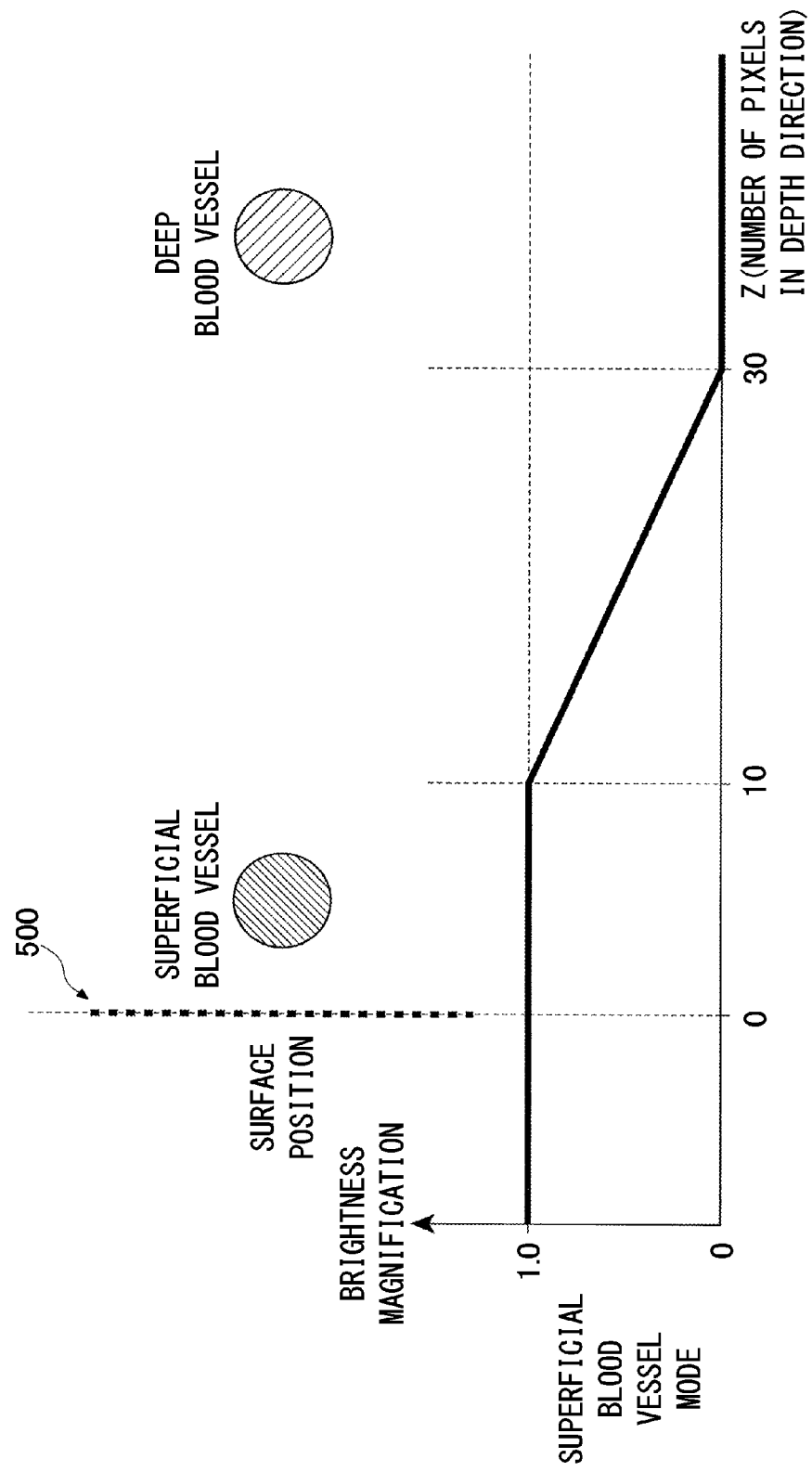
FIG. 15 is a diagram for describing a brightness magnification pattern that the display control unit, which functions in the superficial blood vessel mode, applies to the brightness value of each voxel.

FIG. 15 is a diagram for describing a brightness magnification pattern, that the display control unit 207, which functions in the superficial blood vessel mode, applies to the brightness value of each voxel. The superficial blood vessel mode is executed when the user clicks on the "surface" button in the surface delete field 601 on the user interface screen 600 (see FIG. 13).

As illustrated in FIG. 15, the display control unit 207, which operates in the superficial blood vessel mode, maintains the brightness magnification, used to determine the brightness value of each voxel, at a same magnification from the position of the body surface mask 500 down to a predetermined first depth (e.g. 10 voxels), and then decreases the brightness magnification continuously (or smoothly) down to a predetermined second depth (e.g. 30 voxels), and sets the brightness magnification to 0 for a region deeper than the predetermined second depth.

In the case of the display in the surface blood vessel mode, all that is required is that a sufficient contrast ratio is acquired when visually checked at the first and second depths. Therefore it is preferable that the brightness at the second depth is at least one digit lower than the brightness at the first depth. Other than distinguishing the first depth and the second depth by the brightness intensity, the chromaticity of display may be changed. For example, the first depth may be displayed in red, and the second depth may be displayed in blue. In this case, the tissues and organs can be identified with displaying the first depth information and the second depth information, hence visibility improves.

In Embodiment 1, "continuous" refers to a state where the function corresponding to the change of the brightness magnification continuously changes, and includes a case where the values change discretely, as in the case of digital processing. In FIG. 15, the depth is expressed by a number of pixels (number of voxels), but may be expressed by distance (e.g. mm).

Figure 16:
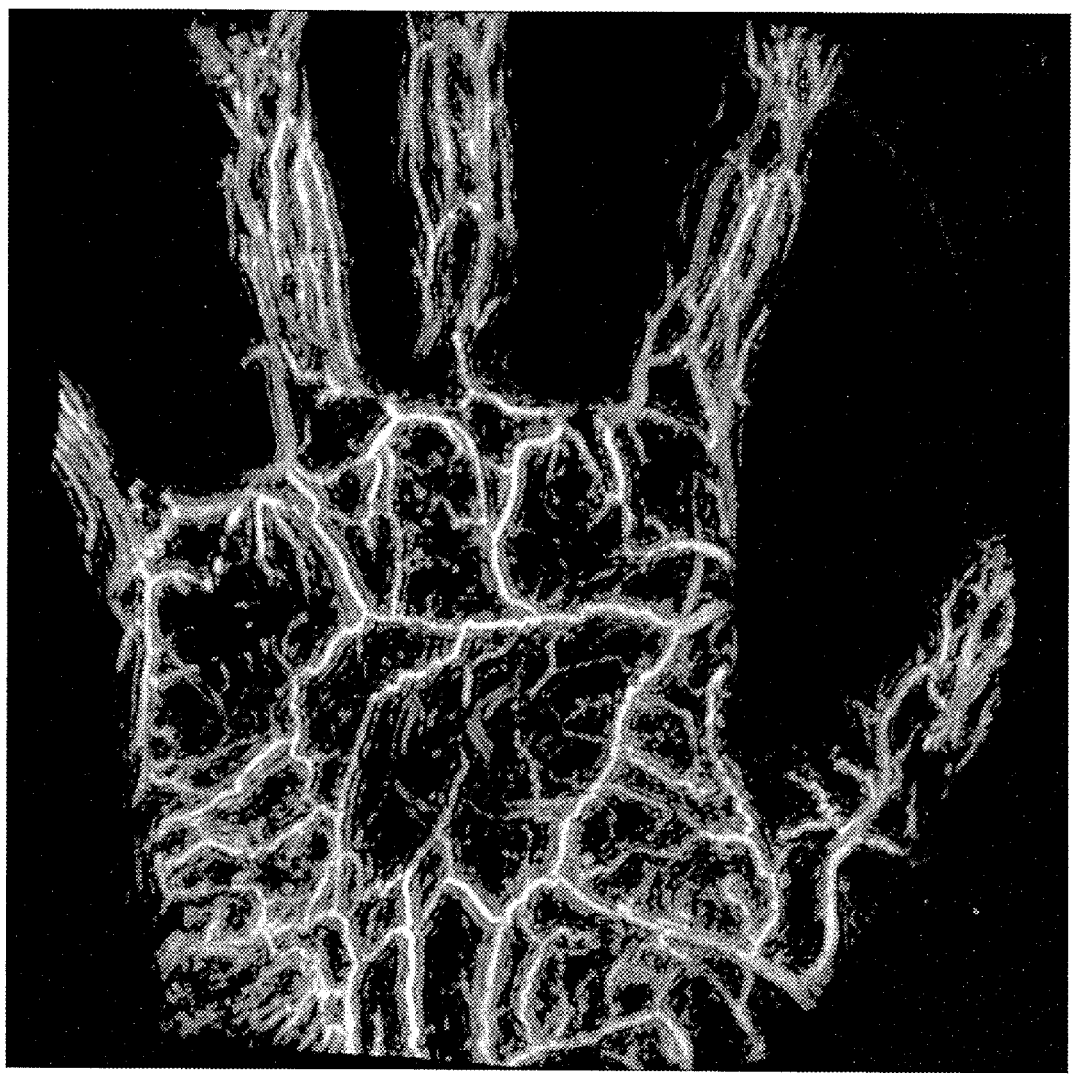
FIG. 16 is a display example of a reconstructed image in the superficial blood vessel mode.

FIG. 16 is a display example of a reconstructed image in the superficial blood vessel mode. In the case of FIG. 16, the reconstructed image is constituted only by superficial blood vessels. This is because, as indicated in FIG. 15, the brightness values of the voxels, which exist in positions deeper than the second depth, are multiplied by 0. Therefore using the display in FIG. 16, the user can accurately confirm only the state of the superficial blood vessels. As indicated in FIG. 15, the brightness magnification is continuously (or smoothly) decreases from the first depth to the second depth. This kind of change is used because display becomes more natural, and the range where the superficial blood vessels exist depends on the individual.

<Screen Example 2>

Figure 17:
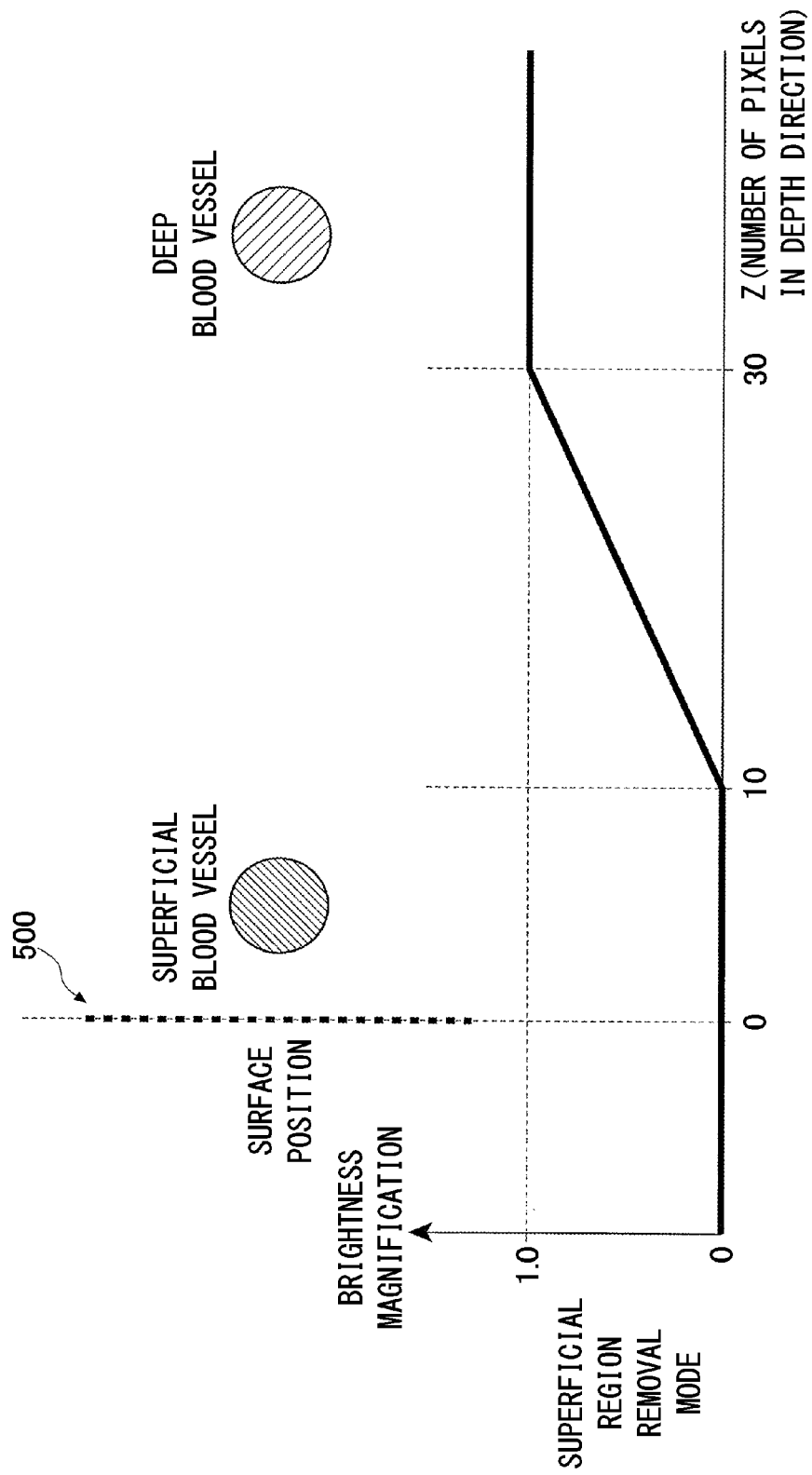
FIG. 17 is a diagram for describing a brightness magnification pattern that the display control unit, which functions in the superficial region removal mode (deep blood vessel mode), applies to the brightness value of each voxel.

FIG. 17 is a diagram for describing a brightness magnification pattern that the display control unit 207, which functions in the superficial region removal mode (deep blood vessel mode), applies to the brightness value of each voxel. The superficial region removal mode is executed when the user clicks on the "Delete" button in the surface delete field 601 on the user interface screen 600 (see FIG. 13).

As illustrated in FIG. 17, the display control unit 207, which operates in the superficial region removal mode, maintains the brightness magnification, used to determine the brightness value to display each voxel, at 0 from the position of the body surface mask 500 down to a predetermined first depth (e.g. 10 voxels), and then increases the brightness magnification continuously (or smoothly) down to a predetermined second depth (e.g. 30 voxels), and sets the brightness magnification to 1 for a region deeper than the predetermined second depth. In FIG. 17 as well, the depth is expressed by a number of pixels (number of voxels), but may be expressed by distance (e.g. mm). In Embodiment 1, the depth direction is the local normal direction (e.g. ±5° range) of the body surface mask 500.

Figure 18:
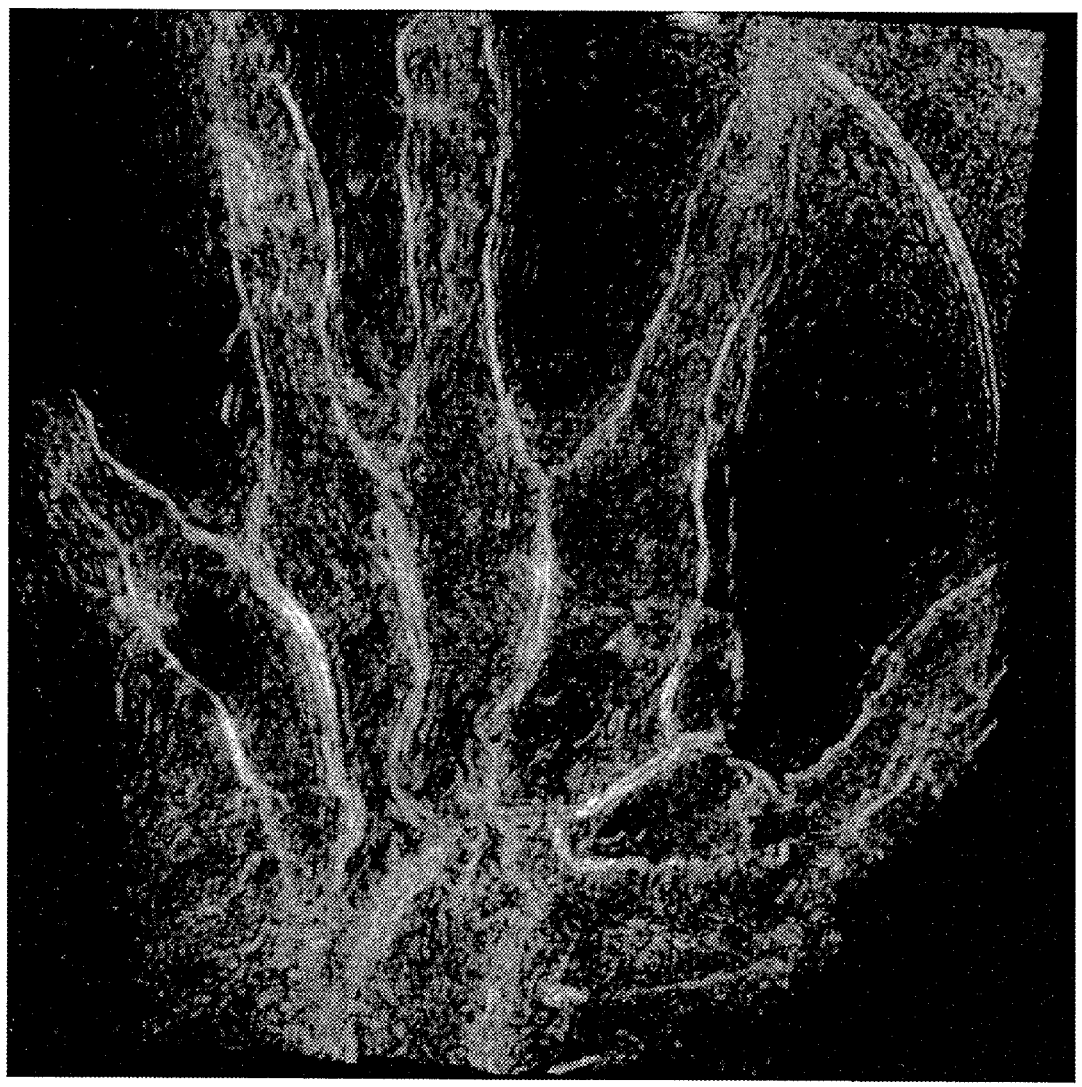
FIG. 18 is a display example of a reconstructed image in the superficial region removal mode (deep blood vessel mode).

FIG. 18 is a display example of a reconstructed image in the superficial region removal mode (deep blood vessel mode). In the case of FIG. 18, the reconstructed image is constructed only by deep blood vessels. This is because, as indicated in FIG. 17, the brightness values of the voxels, which exist in the positions shallower than the first depth, are multiplied by 0. Therefore using the display in FIG. 18, the user can accurately confirm only the state of the deep blood vessels. As indicated in FIG. 17, the brightness magnification continuously (or smoothly) increases from the first depth to the second depth. This kind of change is used because display becomes more natural, and the range where the deep blood vessels exist depend on the individual.

In the case of FIG. 17, the brightness magnification, by which the brightness values of the voxels, which exist in the positions shallower than the first depth, are multiplied, is set to 0, but a value that is greater than 0 and less than 1 may be used for the brightness magnification by which voxels in this region are multiplied. In this case, the deep blood vessels can be observed in the state where the display brightness of the superficial blood vessels is reduced.

Even in this case, however, interpretation of the image of the deep blood vessels is interrupted if the brightness values of the voxels located in the shallow region are high. To prevent this problem, it is preferable to change the brightness magnification by which voxels located in the shallow region is multiplied, so that the display brightness of each voxel located in the shallow region (brightness after the original brightness values are multiplied by the brightness magnification) is less than the maximum value of the display brightness of the voxels located in the deep region (original brightness values in the case of FIG. 17).

Figure 19:
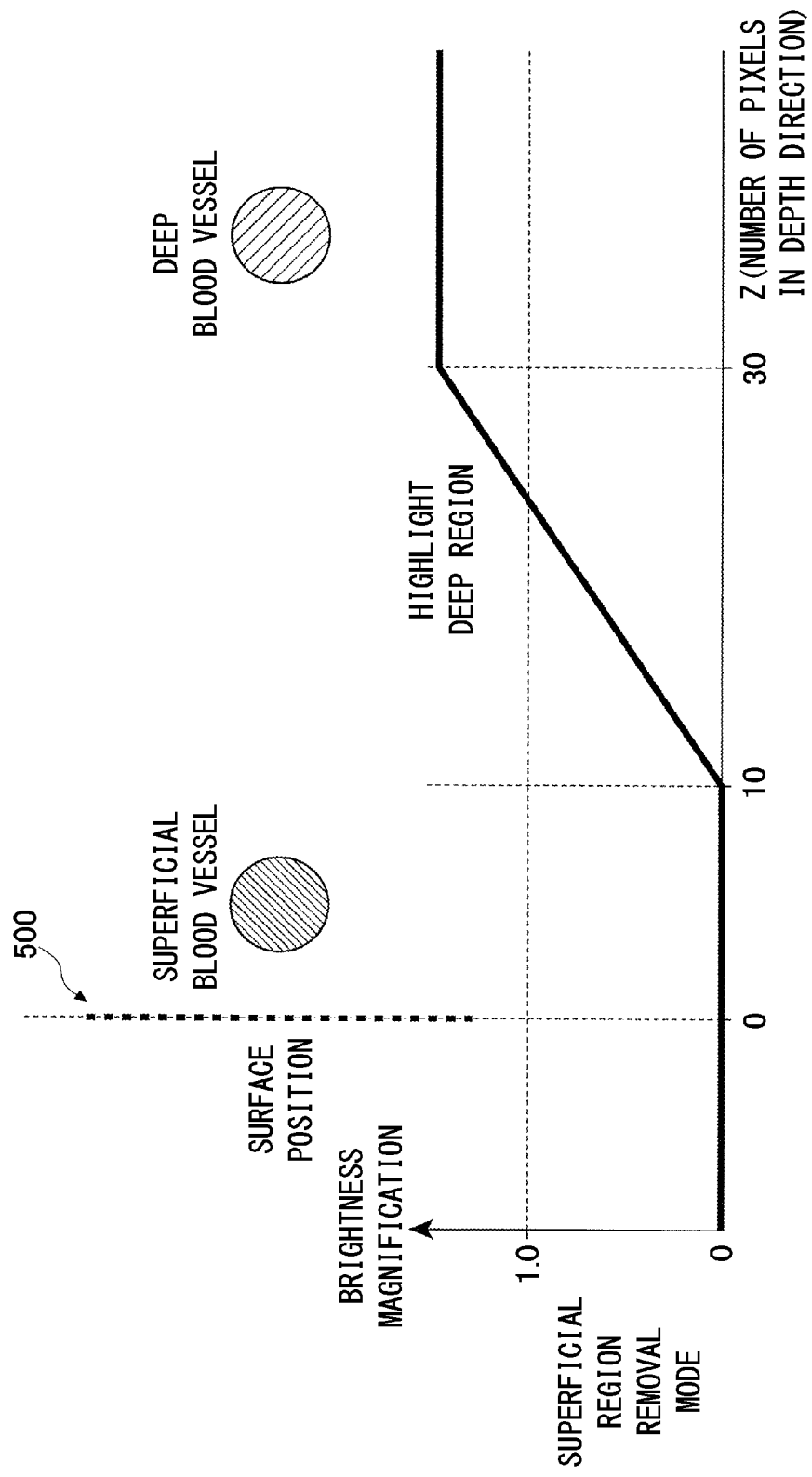
FIG. 19 is a diagram for describing a brightness magnification pattern that the display control unit applies to the brightness value of each voxel when the deep region is highlighted and displayed in the superficial region removal mode (deep blood vessel mode).

In the case of FIG. 17, the brightness magnification, by which the brightness values of voxels located in the deep region are multiplied, is set to 1, but the brightness values of voxels located in the deep region may be highlighted and displayed. FIG. 19 is a diagram for describing a brightness magnification pattern, that the display control unit 207 applies to the brightness value of each voxel when the voxels located in the deep region are highlighted and displayed in the superficial region removal mode (deep blood vessel mode). FIG. 19 is executed when the user inputs the brightness magnification that is greater than 1 in the deep region highlight field 603 in the user interface screen 600 (see FIG. 13). This function may be executed only when there is a check in the check box.

In the case of FIG. 19, the brightness magnification, used to determine the brightness value to display each voxel, is maintained at 0 from the body surface mask 500 to a predetermined first depth (e.g. 10 voxels), as mentioned in FIG. 17, but the brightness magnification in a predetermined second depth (e.g. 30 voxels) is set to a value greater than 1 (e.g. 1.5). The brightness magnification changes continuously (or smoothly) from 0 to 1.5 from the first depth to the second depth. In this case, visibility of the deep blood vessels further improves, and image interpretation of the deep blood vessels becomes easier. This technique can also be applied to the case where the brightness magnification, by which the brightness values of voxels located in a shallow region is multiplied, is set to a value greater than 0 and less than 1, as mentioned above.

<Screen Example 3>

Figure 20:
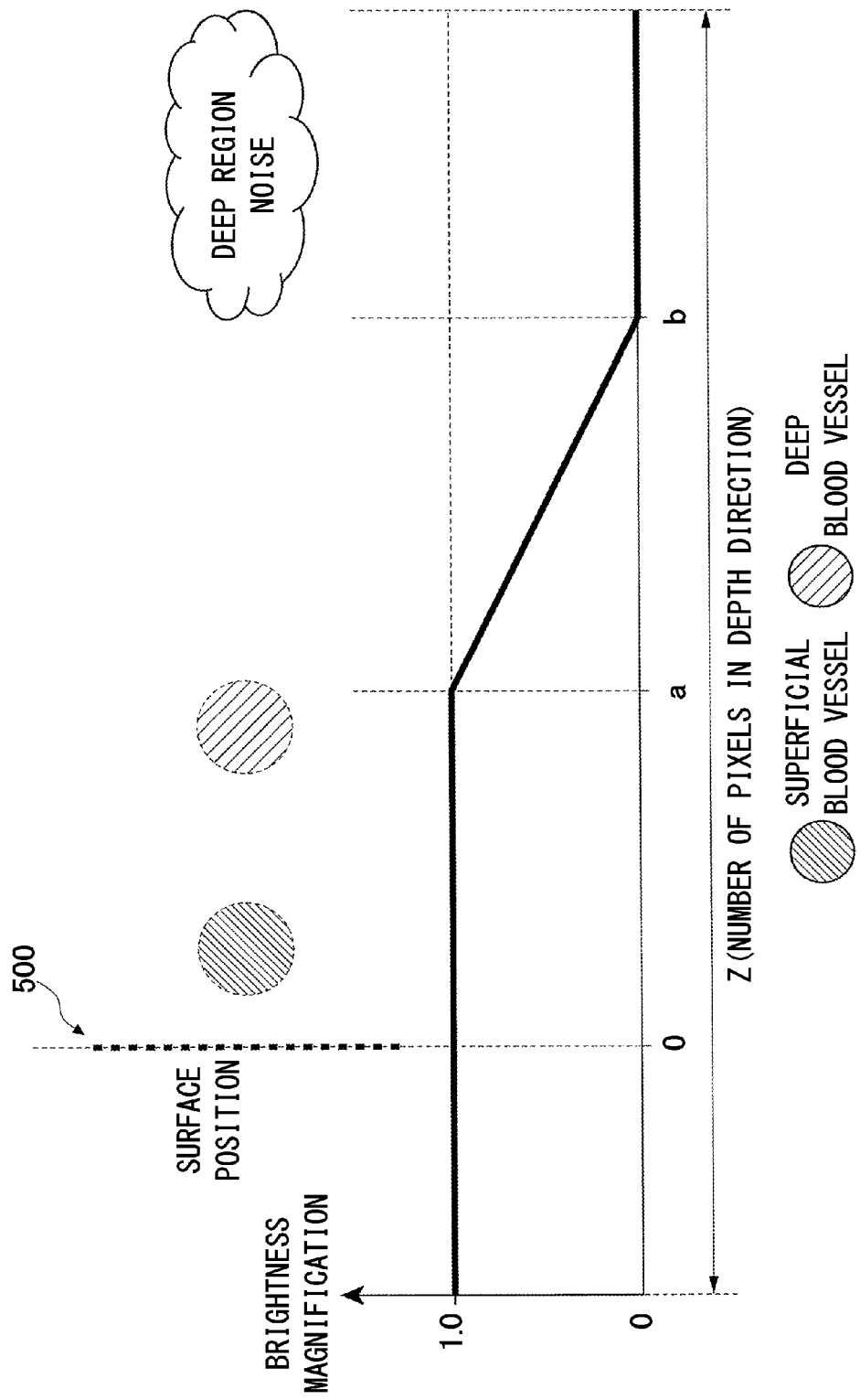
FIG. 20 is a diagram for describing a brightness magnification pattern that the display control unit, which functions in the deep region noise removal mode, applies to the brightness value of each voxel.

FIG. 20 is a diagram for describing a brightness magnification pattern that the display control unit 207, which functions in the bottom noise removal mode, applies to the brightness value of each voxel. The base noise removal mode is executed when the user enters a check the check box in the bottom removal field 604 on the user interface screen 600 (see FIG. 13).

As illustrated in FIG. 20, the display control unit 207, which operates in the bottom noise removal mode, maintains a brightness magnification, used to determine the brightness value of each voxel, at 1 from the position of the body surface mask 500 down to a predetermined first depth a, and then decreases the brightness magnification continuously (or smoothly) down to a predetermined second depth b, and sets the brightness magnification to 1 for a region deeper than the predetermined second depth b. In FIG. 20 as well, the depth is expressed by a number of pixels (number of voxels), but may be expressed by distance (e.g. mm). In Embodiment 1, the first depth a is determined so that both the superficial blood vessels and the deep blood vessels are visually recognized.

Figure 21B:
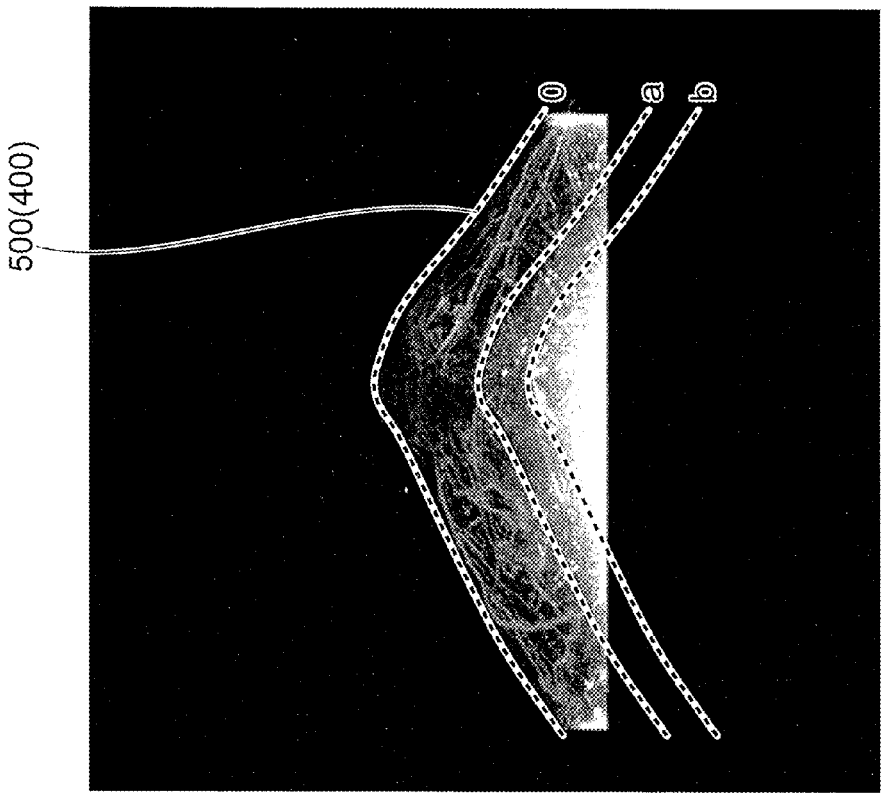
FIG. 21A and FIG. 21B each is a display example of a reconstructed image before removing the bottom noise.
Figure 21A:
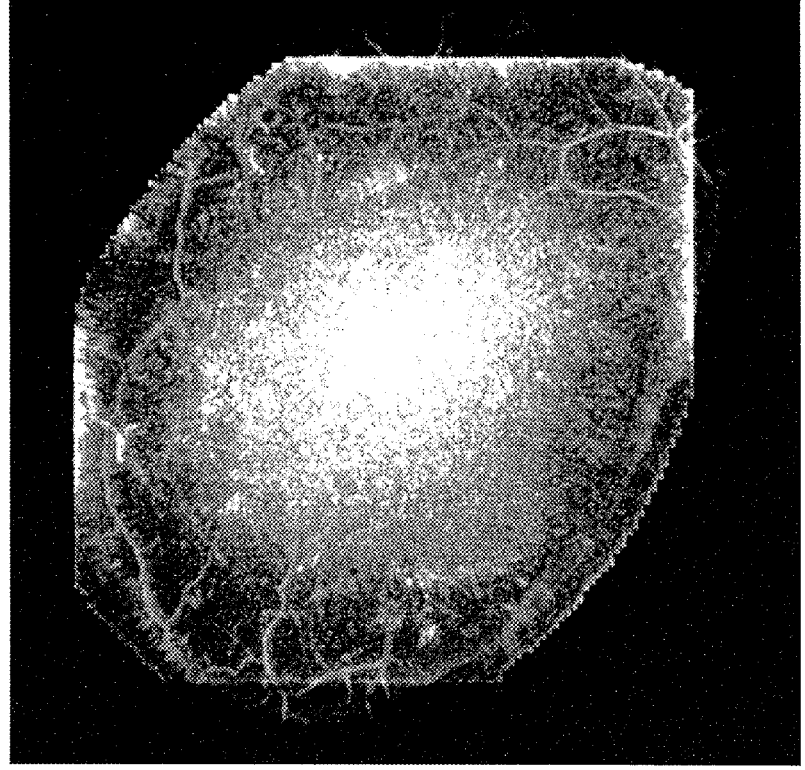

FIG. 21A and FIG. 21B each is a display example of a reconstructed image before removing the bottom noise. The reconstructed images in FIG. 21A and FIG. 21B are display examples when a breast is imaged by the photoacoustic tomography. The image in FIG. 21A corresponds to an image generated by imaging the breast from the front direction of the human body, and the image FIG. 21B corresponds to a cross-sectional image passing the nipple. In the image in FIG. 21A, the bottom noise having high brightness is displayed superimposed on the superficial blood vessels and the deep blood vessels, which interrupts interpretation of the images of the blood vessels. As the image in FIG. 21B indicates, the high brightness voxels are concentrated on the bottom.

Therefore in Embodiment 1, the first depth a, from the position of the body surface mask 500, is determined in accordance with the depth at which the deep blood vessels appear, and the second depth b is determined at the shallowest position of the high brightness voxels. The first depth a and the second depth b here may be provided as initial values in advance, or may be provided while checking the screen.

FIG. 22A and FIG. 22B each is a display example of a reconstructed image after removing the bottom noise. FIG. 22A and FIG. 22B each corresponds to a display example when a check is entered in the check box in the bottom removal field 604. The image in FIG. 22A corresponds to an image generated by imaging the breast from the front direction of the human body, and the image in FIG. 22B corresponds to a cross-sectional image passing the nipple. In the image in FIG. 22A, the base noise has been removed, and the images of the superficial blood vessels and the deep blood vessels can be easily interpreted. As the image in FIG. 22B indicates, the high brightness voxels have been removed.

OTHER EMBODIMENTS

In the above mentioned image processing apparatus 100 according to Embodiment 1, the processing target is the image data in medical fields, particularly the image data acquired by an imaging method in which information of the body surface is limited, but the present invention may be applied to image data handled by computer simulation. If the present invention is used, the processing to estimate the continuous surface, which defines the boundary surface of an object of which outer edge portion is not clear, can be simplified.

In Embodiment 1, cloth simulation is used to estimate the continuous surface, but in the case where the accuracy of the brightness gradient 300 is high, the continuous surface, which defines the boundary surface of the object, may be estimated using the brightness gradient 300.

In Embodiment 1, the continuous surface which defines the body surface of the object is estimated, but the continuous surface which defines the boundary surface that appeared in the internal structure of the object may be estimated.

An example of a method of acquiring volume data by imaging an object by the photoacoustic tomography will be described. The imaging apparatus 120, which images an object by the photoacoustic tomography, may include a light irradiation unit, an ultrasonic probe, a data acquisition system (DAS), a computer, an input unit and a display unit.

The light irradiation unit irradiates light to an object, then an ultrasonic wave is generated inside the object. An ultrasonic wave generated by light based on the photoacoustic effect is also called a photoacoustic wave. The ultrasonic probe receives the photoacoustic wave and outputs an electric signal (photoacoustic signal) which is an analog signal.

The DAS converts an analog signal outputted from the ultrasonic probe into a digital signal, and outputs the digital signal to the computer. The computer stores the digital signal outputted from the DAS as signal data that originated from the photoacoustic wave.

The computer performs signal processing on the stored digital signals, so as to generate volume data which represents the three-dimensional spatial distribution of information on the object (object information). The volume data is stored in the storage unit 105 via the storage unit in the computer and the communication unit 180, based on the storage instruction from the user and the computer.

For the reconstruction algorithm to convert the signal data into volume data (spatial distribution), an analytical reconstruction method, such as a back projection method in the time domain and a back projection method in the Fourier domain, and a model base method (repeated operation method) can be used. For example, for the back projection method in the time domain, universal back projection (UBP), filtered back projection (FBP) and delay-and-sum may be used.

The volume data acquired by the photoacoustic tomography is volume data representing a spatial distribution of at least one object information out of the generation sound pressure (initial sound pressure) of the photoacoustic wave, light absorption energy density, light absorption coefficient, concentration of a substance constituting the object (oxygen saturation degree) and the like.

(Light Irradiation Unit)

The light irradiation unit includes a light source which emits light, and an optical system which guides the light emitted from the light source to an object. The light includes a pulsed light, such as a rectangular wave and triangular wave.

The pulse width of the light emitted from the light source may be a pulse width from 1 ns to 100 ns. The wavelength of the light may be a wavelength in a 400 nm to 1600 nm range. In the case of imaging blood vessels at high resolution, a wavelength of which light is well absorbed by the blood vessels (400 nm to 700 nm) may be used. In the case of imaging a deep region of a living body, a light having a wavelength of which light is not absorbed very much by the background tissue (e.g. water, fat) of the living body (700 nm to 1100 nm) may be used.

For the light source, a laser or light-emitting diode may be used. In the case of using a plurality of wavelengths of lights for measurement, a light source of which wavelength can be changed may be used. In the case of irradiating lights with a plurality of wavelengths to an object, a plurality of light sources, each of which generate a light having mutually different wavelength, may be provided so that each light source irradiates light alternately. Even if a plurality of light sources are used, these light sources are regarded as one light source in this description. For a laser, various lasers, such as a solid-state laser, a gas laser, a dye laser and a semiconductor laser can be used. For example, a pulse laser, such as Nd:YAG laser and an alexandrite laser may be used as the light source. A Ti:Sa laser and an optical parametric oscillator (OPO) laser, which use Nd:YAG laser light as the excitation light, may be used. Further, for the light source 111, a flash lamp or a light-emitting diode may be used. A microwave source may be used for the light source as well.

For the optical system, such optical elements as a lens, a mirror, a prism, an optical fiber, a diffusion plate and a shutter may be used.

The intensity of the light that is allowed to irradiate to a biological tissue, that is, a maximum permissible exposure (MPE), is specified by the following safety standards (IEC 60825-1: Safety of laser products; JIS C6802: Safety standard of laser products; FDA: 21 CFR Part 1040.10; ANSI Z136.1: Laser safety standards and the like). The maximum permissible exposure specifies the intensity of light that is allowed to irradiate in an unit area. This means that more light can be irradiated to an object by irradiating light in a wider area on the surface of the object E all at once, whereby the photoacoustic wave can be received at a higher SN ratio. In the case where the object is a biological tissue (e.g. breast), the emission unit of the optical system may be constituted by a diffusion plate or the like that diffuses light, so that the beam diameter of the high energy light is widened then irradiated. On the other hand, in the case of a photoacoustic microscope, a light-emitting unit of the optical system may be constituted by a lens or the like, so that the beam is focused then irradiated in order to improve resolution.

The light irradiation unit may not include the optical system, and may irradiate light directly from the light source to the object.

(Ultrasonic Probe)

A material constituting the transducer of the ultrasonic probe, a piezoelectric ceramic material such as lead zirconate titanate (PZT), or a high polymer piezoelectric film material such as polyvinylidene fluoride (PVDF) for example, can be used. The transducer may be constituted by an element other than a piezoelectric element. For example, for the transducer, a capacitive micro-machined ultrasonic transducer (CMUT) or an element using a Fabry-Perot interferometer may be used. Any transducer may be used as long as the transducer can output an electric signal by receiving an acoustic wave.

The frequency components constituting the photoacoustic wave are typically 100 KHz to 100 MHz, and the ultrasonic probe that can detect these frequencies may be used as the ultrasonic probe of this invention.

The ultrasonic probe may have a configuration in which a plurality of transducers are disposed on a plane or curved surface, where a 1D array, a 1.5D array, a 1.75D array, a 2D array or the like is formed.

The ultrasonic probe may include an amplifier which amplifies a time series analog signal outputted from the transducer. The ultrasonic probe may include an A/D convertor which converts a time series analog signal outputted from the transducer into a time series digital signal. In other words, the ultrasonic probe may have a function of the DAS.

In order to detect the ultrasonic wave, the acoustic wave and the photoacoustic wave from various angles, it is ideal if the transducers are disposed so as to completely surround the object. If the object is too large to dispose the transducers to completely surround the object, the transducers may be disposed in a hemisphere, so that the object is for the most part surrounded by the transducers.

The positions and the number of transducers may be optimized depending on the object, and all types of ultrasonic probes can be used for the present invention.

The space between the ultrasonic probe and the object may be filled with a medium in which an acoustic wave can propagate. The medium may be a material by which the acoustic characteristics of the object and the ultrasonic probe match at the boundary space there between, and of which transmittance of the ultrasonic wave, acoustic wave and photoacoustic wave is high. For example, water, ultrasonic gel or the like may be used for the medium.

(DAS)

The DAS includes: an amplifier that amplifies an electric signal, which is an analog signal outputted from the transducer; and an A/D convertor that converts an analog signal outputted from the amplifier into a digital signal. The DAS may be constituted by a field programmable gate array (FPGA) chip. The digital signal outputted from the DAS is stored in the storage unit in the computer.

(Computer)

The computer, which functions as a volume data generation unit, includes an operation unit, a storage unit and a control unit. The operation unit may be configured by such processors as a CPU and a graphics processing unit (GPU), and such arithmetic circuits as a field programmable gate array (FPGA) chip. These units may be constituted by a single processor or an arithmetic circuit, or may be constituted by a plurality of processors and arithmetic circuits.

The storage unit may be constituted by a non-transitory storage medium, such as a read only memory (ROM), a magnetic disk or a flash memory. The storage unit may also be a volatile medium, such as a random access memory (RAM). A storage medium which stores programs is a non-transitory storage medium. The storage unit may be constituted of one storage medium, or a plurality of storage media.

The control unit is constituted by an arithmetic element, such as a CPU. The control unit controls the operation of each composing element of the imaging apparatus 120. The control unit may control each composing element of the imaging apparatus 120 based on an instruction signal from the input unit via various operations, such as a measurement start. The control unit also reads program codes stored in the storage unit, and controls the operation of each composing element of the imaging apparatus 120. For example, the control unit may control the emission timing of the light source via the control line. If the optical system includes a shutter, the control unit may control the open/close of the shutter via the control line.

The computer may be a dedicated workstation. Each composing element of the computer may be configured by different hardware. At least a part of the composing elements of the computer may be configured by one hardware component.

(Display Unit)

The display unit is such a display as a liquid crystal display, an organic electroluminescence (EL) FED, a spectacle type display and a head mount display. The display unit is a device which displays an image based on the volume data acquired by a computer, numeric values of a specific position and the like. The display unit may display a GUI for processing an image based on the volume data, and for operating the apparatus. The display unit may be disposed separately from the imaging apparatus 120.

(Input Unit)

For the input unit, an operation console which the user can operate and which is constituted by a mouse and keyboard can be used. The display unit may be configured as a touch panel, and this display unit may be used as the input unit.

The input unit may be configured such that information on a region of interest and the like can be inputted. To input information, numerical values may be inputted, or a slider bar may be operated. Further, an image displayed on the display unit may be updated in accordance with the inputted information. Then the user can set appropriate parameters while checking the image generated by the parameters which were determined by the user operation. The user may operate a remotely disposed input unit of the imaging apparatus 120, so that the information inputted using the input unit is sent to the imaging apparatus 120 via a network.

Each composing element of the imaging apparatus 120 may be configured as an independent apparatus respectively, or may be integrated into one apparatus. Further, at least a part of the composing elements of the imaging apparatus 120 may be integrated into one apparatus.

Information may be transmitted/received among the composing elements of the imaging apparatus 120 via cable or wirelessly.

The control unit 101 of the image processing apparatus 100 may include: a unit which acquires image data of an object including a structure; a unit which acquires information that indicates the position of the structure by performing image processing on the image data; and a unit which estimates a boundary surface of the object by processing using information that indicates the position of the structure. Further, the control unit 101 may use not only information that indicates the position of the structure, but also the image data, to estimate the boundary surface of the object. By taking a plurality of steps: a processing step of acquiring the information that indicates the position of the structure by the image processing on the image data; and a processing step of estimating the boundary surface of the object based on the image data and the information that indicates the position of the structure, the boundary surface of the object can be accurately estimated. Modifications of the method of estimating the boundary surface by the control unit 101 having these units will be described below.

<Modification 1>

In Modification 1, an example of the method where the control unit 101 determines a position of a structure in an object by performing image processing on the volume data of the object will be described.

First, an example of determining a position of a structure (blood vessels) by evaluating the absolute values of the image values of the volume data will be described. The control unit 101 sets a threshold and determines the positions where the image values of the volume data are at least the threshold as the positions of the structure. To set the threshold, it is assumed that the operator sets the threshold by moving the slider bar while checking the image of the volume data displayed on the display unit. Here the slider bar exists in the UI of the application on the display, and is configured such that the bar can be slide by the operation receiving unit 107 (e.g. mouse, keyboard). By changing the threshold using the slider bar, the influence of background tissue, other than the structure, in the image displayed on the display unit, changes. Therefore the operator can specify the threshold when the image of the structure is selectively displayed by moving the slider bar. After specifying the threshold, the operator presses the boundary estimation button existing in the UI, whereby the estimation calculation is started. At this time, the control unit 101 can acquire information on the position of the structure, which is displayed on the display unit, and can use the information to estimate the boundary surface. Instead of using this method, however, the control unit 101 may empirically set a threshold with which the acquired blood vessel image can be discerned, so that the position of the structure (blood vessels) is automatically set. In other words, the control unit 101 may use a threshold that is stored in the storage unit in advance.

The control unit 101 may determine the position of the structure by evaluating the spatial differential value of the image values of the volume data, just like the case of evaluating the absolute value of the image values of the volume data. In other words, the control unit 101 may determine a position where the spatial differential value of the image values of the volume data is at least the threshold as the position of the structure.

The control unit 101 may apply the blood vessel extraction algorithm to the volume data, and determine the position of the extracted blood vessels as the position of the structure. For example, the blood vessel images may be extracted by locally changing the value of the threshold by the adaptive binarization processing, or the blood vessels may be extracted by enhancing the blood vessels using a Hessian matrix or the like after binarization, or the blood vessels may be extracted using a dynamic contour method (e.g. Snake method) or a graph cut method. The Snake method is an image processing method in which the closed curve having the lowest energy among the closed curves surrounding the region is regarded as the boundary surface of the form, and the blood vessel can be extracted by adjusting the coefficient, which determines the tension and rigidity of the closed curve in the energy restriction term. The graph cut method is also an image segmentation method, just like the Snake method, and performs the segmentation of a structure in an object by calculating the minimum cut of the flow of the brightness among each pixel, so as to minimize energy.

Before determining the position of the structure by performing image processing on the volume data, pre-processing to reduce noise (e.g. smoothing processing) may be performed on the volume data. Since this pre-processing decreases the local variation of the image caused by noise, the position of the structure can be more accurately estimated. For the smoothing method, a two-dimensional or three-dimensional averaging filter, a bilateral filter, or such a known method as total variation minimization may be used.

<Modification 2>

In Modification 2, an example of specifying an imaging region so as to determine the parameters of the cloth simulation corresponding to the imaging region will be described.

When the boundary surface is estimated by the cloth simulation, the control unit 101 sets the parameters of the cloth simulation. In the cloth simulation, it is necessary to set parameters, such as the mass m and the length of the spring. The control unit 101 can set the parameters of the cloth simulation using information that indicates the imaging region.

For example, if the imaging region is a breast, in many regions blood vessel images sparsely exist compared with a palm. In this case, if the mass of the mass point in the cloth simulation is too heavy or if the length of the spring is too short, the boundary surface estimated in a region where blood vessels do not exist may differ from the actual boundary surface. Therefore when the information, that indicates the imaging region is a breast, is received, the control unit 101 sets the empirically acquired parameter values appropriate for the breast. The parameter values may be calculated under constraint conditions, so that the surface does not become overly irregular, and the surface profile of the cloth simulation becomes smooth.

A table that indicates the relationship between a plurality of imaging regions and the parameters corresponding to each imaging region may be stored in the storage unit. In this case, the control unit 101 may acquire information that indicates the imaging region, and read the parameters corresponding to the imaging region from the table.

When the imaging region is a breast, it is preferable that the mass of the mass point in the cloth simulation is lighter than that in the case when the imaging region is a palm. When the imaging region is a breast, it is preferable that the length of the spring in the cloth simulation is longer than in the case when the imaging region is a palm.

If the operator specifies an imaging region using the operation receiving unit 107, the control unit 101 can acquire information that indicates the imaging region via the operation receiving unit 107. The operator may specify the imaging region using the UI.

<Modification 3>

In Modification 3, an example of processing that decreases images that may negatively influence the estimation of the boundary surface from the volume data will be described.

If a strong artifact or image other than the object exists in the volume data, estimation of the boundary surface may be negatively influenced. For example, if a strong artifact exists in an area other than the boundary surface when the boundary surface is estimated by the cloth simulation, the cloth is hooked to this artifact, and a position that is different from the boundary surface may be defined as the boundary surface.

The operator can specify a region which may negatively influence the estimation of the boundary surface using the operation receiving unit 107 while checking the image of the volume data displayed on the display unit. The control unit 101 can decrease or delete the image values in the specified region. Here the target of which image values are decreased is determined by manually inputting the target, but the control unit 101 may determine the target of which image values are decreased by performing image processing on the volume data. Further, the control unit 101 may perform the pre-processing to reduce noise (e.g. smoothing) first, then may determine the target of which image values are decreased by performing image processing on the volume data.

<Modification 4>

In Modification 4, an example of using the information that indicates the estimated boundary surface for processing to generate the volume data again, or for processing to correct the volume data, will be described.

The control unit 101 can determine the boundary at which the sound velocity changes, using the information that indicates the estimated boundary surface. When the object and the acoustic matching material (e.g. water) form a boundary surface, the control unit 101 assigns the sound velocity of the object to the object side of the boundary surface, and assigns the sound velocity of the acoustic matching material to the acoustic matching material side of the boundary surface. Then the control unit 101 performs the reconstruction processing using the assigned sound velocity distribution, whereby the volume data is generated.

If at least one of the sound velocities of the object and the acoustic matching material is unknown, the sound velocity is estimated for each region on each side of the boundary surface, regarding the estimated boundary surface as the boundary of the sound velocity distribution. The method of estimating the sound velocity may be a known method. For example, the control unit 101 assigns the sound velocity to each region on each side of the boundary surface, and estimates, as the optimum sound velocity, a sound velocity when the total of the edges of the image generated by reconstructing each region using the assigned sound velocity is the maximum.

As described above, the sound velocity distribution can be accurately set by using the information that indicates the estimated boundary surface.

The control unit 101 can determine the light quantity distribution inside the object using the information that indicates the estimated boundary surface. The control unit 101 can also correct a variation of the image values of the volume data, caused by a variation of the light quantity, using the information that indicates the light quantity distribution inside the object.

For example, the control unit 101 projects the light quantity profile of the irradiated light to a position of the estimated boundary surface, whereby the light quantity profile at the position of the boundary surface can be determined. The control unit 101 sets the light quantity profile at the position of the boundary surface as the emitted light quantity of a virtual light source at the boundary surface, and calculates the propagation of the light generated from the virtual light source. The light quantity distribution inside the object can be calculated like this using the information that indicates the estimated boundary surface. Then by correcting the variation of the images of the volume data using the calculated light quantity distribution, the control unit 101 can accurately generate the volume data, including the light absorption coefficient and oxygen saturation degree.

Embodiments of the present invention have been described, but the technical scope of the present invention is not limited to the description of the embodiments. As the claims indicate, various changes and modifications of the embodiments are included in the technical scope of the present invention.

The present invention may be implemented by executing the following processing. That is, a program to implement at least one function of the above-mentioned embodiments is supplied to a system or apparatus via a network or various storage media, and at least one processor of the computer of the system or apparatus reads and executes the program. The present invention may also be implemented by a circuit (e.g. ASIC, FPGA), which implements at least one function of the above embodiments.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image processing apparatus comprising:
   a memory storing a program; and
   one or more processors that, by executing the program, function as a plurality of units comprising:
   (1) an acquisition unit that acquires (a) photoacoustic volume data by imaging an object and (b) a brightness value of a voxel group constituting the photoacoustic volume data; and
   (2) an estimating unit that estimates, based on the brightness value of the voxel group constituting the photoacoustic volume data, a continuous surface which defines a boundary surface of the object,
   wherein the estimating unit (a) arranges a cloth model from a certain direction to superficial vessels in the object identified by the brightness value of the voxel group constituting the photoacoustic volume data and (b) estimates the continuous surface by deforming the cloth model so that a catenary is formed between the superficial vessels.

2. The image processing apparatus according to claim 1, wherein the plurality of units further comprises a display control unit that displays the continuous surface superimposed on the volume data.

3. The image processing apparatus according to claim 1, wherein the plurality of units further comprises a display control unit that changes a brightness magnification, which is used for displaying the brightness value of each voxel, in accordance with the depth from the continuous surface.

4. The image processing apparatus according to claim 3, wherein the display control unit changes the brightness magnification so that all the displayed brightness values of the voxels located in a shallow region are smaller than the maximum value of the displayed brightness values of the voxels located in a deep region.

5. The image processing apparatus according to claim 1, wherein the estimating unit applies a physical model, which allows a lattice point group, formed by mutually connecting each lattice point having mass via springs, to freely fall from an area above the object due to gravity, to a distribution of a brightness gradient, so as to estimate the continuous surface.

6. The image processing apparatus according to claim 5, wherein the estimating unit determines the normal direction of each voxel based on the distribution of the brightness gradient, and uses the normal direction as a direction of resistance that acts on the physical model.

7. The image processing apparatus according to claim 1, wherein the estimating unit estimates the continuous surface by processing the voxels having a brightness value exceeding a noise level determined in advance.

8. The image processing apparatus according to claim 7, wherein the estimating unit receives specification of the noise level via an input field disposed on a user interface screen.

9. The image processing apparatus according to claim 1, wherein the plurality of units further comprises a display control unit that displays a button, to remove high brightness voxels existing in a deep region of the volume data from the display target, on a user interface screen.

10. The image processing apparatus according to claim 1, wherein the volume data is one of photo-acoustic tomographic image data, ultrasonic image data, and MRI angiographic image data.

11. The image processing apparatus according to claim 1, wherein in the case when the voxels constituting the volume data are rearranged in descending order of brightness value, and the ratio of a voxel set on the lower brightness side to the entire volume data is a predetermined value or less, the estimating unit determines a brightness gradient for brightness values normalized by the maximum brightness value in the voxel set.

12. The image processing apparatus according to claim 11, wherein the predetermined value is a value that is at least 99% and not more than 99.99%.

13. The image processing apparatus according to claim 1, having a function to display the object, with changing the chromaticity of the voxels in the direction from the continuous surface, which defines the boundary surface of the object, to inside the object.

14. The image processing apparatus according to claim 5, wherein the estimating unit acquires information that indicates the imaged region, and sets at least one of the mass of the lattice point and the length of the spring based on the information that indicates the imaged region.

15. An image processing apparatus comprising:
   a memory storing a program; and
   one or more processors that, by executing the program, function as a plurality of units comprising:
   (1) a unit that acquires photoacoustic volume data of an object including a structure;

(2) a unit that acquires information which indicates the position of the structure by image processing on the photoacoustic volume data; and
(3) a unit that estimates a boundary surface of the object by processing using the information which indicates the position of the structure,
wherein the unit that estimates the boundary surface (a) arranges a cloth model from a certain direction to superficial vessels in the object identified by a brightness value of the information which indicates the position of the structure and (b) estimates the boundary surface by deforming the cloth model so that a catenary is formed between the superficial vessels.

16. The image processing apparatus according to claim 15, wherein the unit that estimates the boundary surface applies a physical model, which allows a lattice point group, formed by mutually connecting each lattice point having mass via springs, to freely fall from an area above the object due to gravity, to a distribution of a brightness gradient, so as to estimate the continuous surface.

17. An image processing method comprising:
processing that acquires (a) photoacoustic volume data by imaging an object and (b) a brightness value of a voxel group constituting the photoacoustic volume data; and
processing that estimates, based on the brightness value of the voxel group constituting the photoacoustic volume data, a continuous surface which defines a boundary surface of the object,
wherein the processing that estimates the continuous surface (a) arranges a cloth model from a certain direction to superficial vessels in the object identified by the brightness value of the voxel group constituting the photoacoustic volume data and (b) estimates the continuous surface by deforming the cloth model so that a catenary is formed between the superficial vessels.

18. The image processing method according to claim 17, wherein the processing that estimates the continuous surface applies a physical model, which allows a lattice point group, formed by mutually connecting each lattice point having mass via springs, to freely fall from an area above the object due to gravity, to a distribution of a brightness gradient, so as to estimate the continuous surface.

19. A non-transitory computer-readable storage medium having a program stored therein, the program allowing a computer to execute the image processing method according to claim 17.

20. The image processing apparatus according to claim 1, wherein the estimating unit estimates the continuous surface formed by the cloth model as a body surface of the object.

21. The image processing apparatus according to claim 1, wherein the plurality of units further comprises a display control unit that controls display of the continuous surface estimated by the estimating unit, the continuous surface being superimposed on the volume data.

22. The image processing apparatus according to claim 1, wherein the superficial vessels are identified by the brightness value of the voxel group constituting the volume data, and
wherein the estimating unit deforms the cloth model such that a catenary is formed between the superficial vessels.

23. The image processing apparatus according to claim 1, wherein the estimating unit disposes the cloth model in a position above the superficial vessels, which indicate high brightness values in the voxel data, and deforms the cloth model such that a catenary is formed between the superficial vessels.

* * * * *